(12) United States Patent
Kubota et al.

(10) Patent No.: US 11,480,813 B2
(45) Date of Patent: Oct. 25, 2022

(54) PROJECTION OF DEFOCUSED IMAGES ON THE PERIPHERAL RETINA TO TREAT REFRACTIVE ERROR

(71) Applicant: ACUCELA INC., Seattle, WA (US)

(72) Inventors: Ryo Kubota, Seattle, WA (US); Nabin Joshi, New York City, NY (US); Arkady Selenow, New York City, NY (US); Steven Ali, New York City, NY (US); Stefan Bauer, Bern (CH); Jean-Noël Fehr, Neuchâtel (CH); Moritz Haeberli, Zürich (CH); Patrizia Weber, Bern (CH); Julien Sauvet, Biel (CH); Amitava Gupta, Roanoke, VA (US)

(73) Assignee: ACUCELA INC., Seattle, WA (US)

( * ) Notice: Subject to any disclaimer, the term of this patent is extended or adjusted under 35 U.S.C. 154(b) by 0 days.

(21) Appl. No.: 17/650,134

(22) Filed: Feb. 7, 2022

(65) Prior Publication Data
US 2022/0155616 A1     May 19, 2022

Related U.S. Application Data

(63) Continuation of application No. 17/304,691, filed on Jun. 24, 2021, now Pat. No. 11,275,259, which is a
(Continued)

(51) Int. Cl.
*G02C 7/02*     (2006.01)
*G02C 7/04*     (2006.01)
(Continued)

(52) U.S. Cl.
CPC .......... *G02C 7/022* (2013.01); *A61B 3/0008* (2013.01); *A61B 3/0058* (2013.01); *A61F 9/00* (2013.01);
(Continued)

(58) Field of Classification Search
CPC ...... G02C 7/022; G02C 2202/24; G02C 7/04; G02C 7/06; A61B 3/0008; A61B 3/0058; A61B 3/10; A61F 9/00; A61F 9/0017
(Continued)

(56) References Cited

U.S. PATENT DOCUMENTS

| | | |
|---|---|---|
| 6,516,808 B2 | 2/2003 | Schulman |
| 7,018,040 B2 | 3/2006 | Blum |

(Continued)

FOREIGN PATENT DOCUMENTS

| | | |
|---|---|---|
| EP | 3413116 | 12/2018 |
| KR | 20180038359 A | 4/2018 |

(Continued)

OTHER PUBLICATIONS

Adler, Daniel, et al., "The possible effect of under correction on myopic progression in children," Clin Exp Optom., 89:315-321 (2006).

(Continued)

*Primary Examiner* — Jordan M Schwartz
(74) *Attorney, Agent, or Firm* — FisherBroyles LLP; John Shimmick

(57) ABSTRACT

An apparatus to treat refractive error of the eye comprises one or more optics configured to project stimuli comprising out of focus images onto the peripheral retina outside the macula. While the stimuli can be configured in many ways, in some embodiments the stimuli are arranged to decrease interference with central vison such as macular vision. The stimuli can be out of focus images may comprise an amount of defocus within a range from about 3 Diopters ("D") to about 6 D. In some embodiments, the brightness of the stimuli is greater than a brightness of background illumination by an appropriate amount such as at least 3 times the background brightness. In some embodiments, each of a (Continued)

plurality of stimuli comprises a spatial frequency distribution with an amplitude profile having spatial frequencies within a range from about range of $1 \times 10^{-1}$ to $2.5 \times 10^{1}$ cycles per degree.

17 Claims, 19 Drawing Sheets

Related U.S. Application Data continuation of application No. PCT/US2021/036100, filed on Jun. 7, 2021.

(60) Provisional application No. 62/706,456, filed on Aug. 18, 2020, provisional application No. 62/706,153, filed on Aug. 3, 2020, provisional application No. 63/036,226, filed on Jun. 8, 2020.

(51) Int. Cl.
*A61B 3/00* (2006.01)
*A61F 9/00* (2006.01)
*G02C 7/06* (2006.01)
*G02C 11/04* (2006.01)

(52) U.S. Cl.
CPC .............. *A61F 9/0017* (2013.01); *G02C 7/04* (2013.01); *G02C 7/06* (2013.01); *G02C 11/04* (2013.01); *G02C 2202/24* (2013.01)

(58) Field of Classification Search
USPC ........................................................ 351/203
See application file for complete search history.

(56) References Cited

U.S. PATENT DOCUMENTS

| | | |
|---|---|---|
| 8,246,167 B2 | 8/2012 | Legerton |
| 8,432,124 B2 | 4/2013 | Foster |
| 8,662,664 B2 | 3/2014 | Artal Soriano |
| 8,857,983 B2 | 10/2014 | Pugh |
| 8,960,898 B1 * | 2/2015 | Etzkorn .................. G02C 7/101 351/159.03 |
| 9,345,813 B2 | 5/2016 | Hogg |
| 9,763,827 B2 | 9/2017 | Kelleher |
| 9,885,884 B2 | 2/2018 | Drobe |
| 9,918,894 B2 | 3/2018 | Lam |
| RE47,006 E | 8/2018 | To |
| 10,133,092 B2 | 11/2018 | Tsubota |
| 10,146,067 B2 | 12/2018 | Tsai |
| 10,231,897 B2 | 3/2019 | Tse |
| 10,268,050 B2 | 4/2019 | To |
| 10,274,731 B2 * | 4/2019 | Maimone ................ G06F 3/011 |
| 10,288,909 B1 | 5/2019 | Youssef |
| 10,788,686 B2 | 9/2020 | Tsai |
| 10,884,264 B2 | 1/2021 | Hones |
| 10,921,612 B2 | 2/2021 | Zhou |
| 10,993,515 B1 | 5/2021 | Kim |
| 11,000,186 B2 | 5/2021 | Linder |
| 11,163,166 B1 | 11/2021 | Ebert |
| 11,187,921 B2 | 11/2021 | Zhou |
| 11,275,259 B2 * | 3/2022 | Kubota .................. G02C 11/04 |
| 2002/0186345 A1 | 12/2002 | Duppstadt |
| 2003/0011745 A1 | 1/2003 | Molebny |
| 2004/0237971 A1 | 12/2004 | Radhakrishnan |
| 2004/0246441 A1 | 12/2004 | Stark |
| 2004/0257529 A1 | 12/2004 | Thomas |
| 2006/0082729 A1 | 4/2006 | To |
| 2007/0002452 A1 | 1/2007 | Munro |
| 2007/0076217 A1 | 4/2007 | Baker |
| 2007/0115431 A1 | 5/2007 | Smith, III |
| 2007/0127349 A1 | 6/2007 | Hotta |
| 2008/0291391 A1 | 11/2008 | Meyers |
| 2008/0309882 A1 | 12/2008 | Thorn |
| 2009/0002631 A1 | 1/2009 | Campbell |
| 2009/0187242 A1 | 7/2009 | Weeber |
| 2009/0204207 A1 | 8/2009 | Blum |
| 2010/0076417 A1 | 3/2010 | Suckewer |
| 2010/0296058 A1 | 11/2010 | Ho |
| 2011/0085129 A1 | 4/2011 | Legerton |
| 2011/0109878 A1 * | 5/2011 | Klink ..................... A61B 3/112 351/205 |
| 2011/0153012 A1 | 6/2011 | Legerton |
| 2011/0157554 A1 | 6/2011 | Kawai |
| 2011/0202114 A1 | 8/2011 | Kessel |
| 2012/0199995 A1 | 8/2012 | Pugh |
| 2012/0206485 A1 | 8/2012 | Osterhout |
| 2012/0212399 A1 | 8/2012 | Border |
| 2012/0215291 A1 | 8/2012 | Pugh |
| 2013/0027655 A1 | 1/2013 | Blum |
| 2013/0278887 A1 | 10/2013 | Legerton |
| 2014/0039048 A1 | 2/2014 | Bavik |
| 2014/0039361 A1 | 2/2014 | Siu |
| 2014/0194773 A1 | 7/2014 | Pletcher |
| 2014/0218647 A1 | 8/2014 | Blum |
| 2014/0240665 A1 | 8/2014 | Pugh |
| 2014/0268029 A1 | 9/2014 | Pugh |
| 2014/0277291 A1 | 9/2014 | Pugh |
| 2015/0057701 A1 | 2/2015 | Kelleher |
| 2015/0109574 A1 | 4/2015 | Tse |
| 2015/0160477 A1 | 6/2015 | Dai |
| 2015/0241706 A1 | 8/2015 | Schowengerdt |
| 2015/0312560 A1 * | 10/2015 | Deering ................ G02B 13/16 345/1.3 |
| 2016/0056498 A1 | 2/2016 | Flitsch |
| 2016/0067037 A1 | 3/2016 | Rosen |
| 2016/0091737 A1 | 3/2016 | Kim |
| 2016/0143801 A1 | 5/2016 | Lam |
| 2016/0158486 A1 | 6/2016 | Colbaugh |
| 2016/0212404 A1 | 7/2016 | Maiello |
| 2016/0270656 A1 | 9/2016 | Samec |
| 2016/0377884 A1 | 12/2016 | Lau |
| 2017/0000326 A1 | 1/2017 | Samec |
| 2017/0001032 A1 | 1/2017 | Samec |
| 2017/0010480 A1 | 1/2017 | Blum |
| 2017/0014074 A1 | 1/2017 | Etzkorn |
| 2017/0055823 A1 | 3/2017 | Lu |
| 2017/0072218 A1 | 3/2017 | Rucker |
| 2017/0097519 A1 | 4/2017 | Lee |
| 2017/0184875 A1 | 6/2017 | Newman |
| 2017/0229730 A1 | 8/2017 | Flitsch |
| 2017/0236255 A1 | 8/2017 | Wetzstein |
| 2017/0270636 A1 | 9/2017 | Shtukater |
| 2017/0276963 A1 | 9/2017 | Brennan |
| 2017/0307779 A1 | 10/2017 | Marullo |
| 2018/0017810 A1 | 1/2018 | Wu |
| 2018/0017814 A1 | 1/2018 | Tuan |
| 2018/0052319 A1 | 2/2018 | McCabe |
| 2018/0055351 A1 | 3/2018 | Yates |
| 2018/0074322 A1 | 3/2018 | Rousseau |
| 2018/0090958 A1 | 3/2018 | Steger |
| 2018/0092738 A1 | 4/2018 | Tai |
| 2018/0136486 A1 | 5/2018 | MacNamara |
| 2018/0161231 A1 | 6/2018 | Tse |
| 2018/0173010 A1 | 6/2018 | Harant |
| 2018/0188556 A1 | 7/2018 | Portney |
| 2018/0221140 A1 | 8/2018 | Rosen |
| 2018/0275427 A1 | 9/2018 | Lau |
| 2018/0345034 A1 | 12/2018 | Butzloff |
| 2019/0033618 A1 | 1/2019 | Choi |
| 2019/0033619 A1 | 1/2019 | Neitz |
| 2019/0038123 A1 * | 2/2019 | Linder .................. G02C 11/10 |
| 2019/0049730 A1 | 2/2019 | Miller |
| 2019/0076241 A1 | 3/2019 | Alarcon Heredia |
| 2019/0107734 A1 | 4/2019 | Lee |
| 2019/0113757 A1 | 4/2019 | Van Heugten |
| 2019/0129204 A1 | 5/2019 | Tsubota |
| 2019/0227342 A1 | 7/2019 | Brennan |
| 2019/0235279 A1 | 8/2019 | Hones |
| 2019/0247675 A1 | 8/2019 | Legerton |
| 2019/0250432 A1 | 8/2019 | Kim |
| 2019/0314147 A1 | 10/2019 | Blum |
| 2020/0033637 A1 | 1/2020 | Jamshidi |

(56) References Cited

U.S. PATENT DOCUMENTS

| | | |
|---|---|---|
| 2020/0089023 A1 | 3/2020 | Zhou |
| 2020/0110265 A1 | 4/2020 | Serdarevic |
| 2020/0133024 A1 | 4/2020 | Paune Fabre |
| 2020/0142219 A1 | 5/2020 | Rousseau |
| 2020/0183169 A1 | 6/2020 | Peng |
| 2020/0360184 A1 | 11/2020 | Xiao |
| 2021/0018762 A1 | 1/2021 | Zheleznyak |
| 2021/0031051 A1 | 2/2021 | Kubota |
| 2021/0048690 A1 | 2/2021 | Guillot |
| 2021/0069524 A1 | 3/2021 | Kubota |
| 2021/0263336 A1 | 8/2021 | Gupta |
| 2021/0298440 A1 | 9/2021 | Kim |
| 2021/0356767 A1 | 11/2021 | Kubota |
| 2021/0379399 A1 | 12/2021 | Buscemi |
| 2021/0382325 A1 | 12/2021 | Kubota |
| 2021/0382326 A1 | 12/2021 | Kubota |
| 2021/0389607 A1 | 12/2021 | Buscemi |

FOREIGN PATENT DOCUMENTS

| | | |
|---|---|---|
| WO | 2009074638 A3 | 6/2009 |
| WO | 2009121810 | 10/2009 |
| WO | 2010043599 | 4/2010 |
| WO | 2011089042 | 7/2011 |
| WO | 2012136470 | 10/2012 |
| WO | 2013087518 | 6/2013 |
| WO | 2014033035 | 3/2014 |
| WO | 2014191460 | 12/2014 |
| WO | 2015063097 | 5/2015 |
| WO | 2015186723 | 12/2015 |
| WO | 2015192117 | 12/2015 |
| WO | 2018014712 | 1/2018 |
| WO | 2018014960 | 1/2018 |
| WO | 2018085576 | 5/2018 |
| WO | 2018208724 | 11/2018 |
| WO | 2019114463 | 6/2019 |
| WO | 2019191510 | 10/2019 |
| WO | 2019217241 | 11/2019 |
| WO | 2020014074 | 1/2020 |
| WO | 2020014613 | 1/2020 |
| WO | 2020028177 | 2/2020 |
| WO | 2020069232 | 4/2020 |
| WO | 2021022193 | 2/2021 |
| WO | 2021056018 | 3/2021 |
| WO | 2021168481 | 8/2021 |
| WO | 2021231684 | 11/2021 |
| WO | 2021252318 | 12/2021 |
| WO | 2021252319 | 12/2021 |
| WO | 2021252320 | 12/2021 |

OTHER PUBLICATIONS

Aleman, Andrea C., et al.,, "Reading and Myopia: Contrast Polarity Matters," Scientific Reports, 8 pages (2018).

Arden, G.B., et al., "Does dark adaptation exacerbate diabetic retinopathy? Evidence and a linking hypothesis," Vision Research 38:1723-1729 (1998).

Arden, GB, et al, "Regression of early diabetic macular edema is associated with prevention of dark adaptation", in Eye, (2011). 25, pp. 1546-1554.

Benavente-Perez, A., et al., "Axial Eye Growth and Refractive Error Development Can Be Modified by Exposing the Peripheral Retina to Relative Myopic or Hyperopic Defocus," Invest Ophthalmol Vis Sci., 55:6765-6773 (2014).

Bonar, JR, et al., "High brightness low power consumption microLED arrays", in SPIE DigitalLibrary.org/conference-proceedings-of-spie, SPIE OPTO, 2016, San Francisco, California, United States, Abstract Only.

Carr, Brittany J., et al., "The Science Behind Myopia," retrieved from https://webvision.med.utah.edu/book/part-xvii-refractive-errors/the-science-behind-myopia-by-brittany-j-carr-and-william-k-stell/, 89 pages (2018).

Chakraborty, R., et al., "Diurnal Variations in Axial Length, Choroidal Thickness, Intraocular Pressure, and Ocular Biometrics," IOVS, 52(8):5121-5129 (2011).

Chakraborty, R., et al., "Hyperopic Defocus and Diurnal Changes in Human Choroid and Axial Length," Optometry and Visual Science, 90(11):1187-1198 (2013).

Chakraborty, R., et al., "Monocular Myopic Defocus and Daily Changes in Axial Length and Choroidal Thickness of human Eyes," Exp Eye Res, 103:47-54 (2012).

Cooper, J., et al., "Current status of the development and treatment of myopia", Optometry, 83:179-199 (2012).

Cooper, J., et al., "A Review of Current Concepts of the Etiology and Treatment of Myopia," Eye & Contact Lens, 44(4):231-247 (Jul. 2018).

Demory, B., et al., "Integrated parabolic microlenses on micro LED color pixels", in Nanotechnology, (2018); 29, 16, pp. 1018, Abstract Only.

Dolgin, Elie, "The Myopia Boom," Nature 519:276-278 (2015).

Edrington, Timothy B., "A literature review: The impact of rotational stabilization methods on toric soft contact lens performance," Contact Lens & Anterior Eye, 34:104-110 (2011).

Flitcroft, D.I., "The complex interactions of retinal, optical and environmental factors in myopia aetiology," 31(6):622-660 (2012).

Garner, L.F., et al., "Crystalline Lens Power in Myopia," Optometry and Vision Science, 69:863-865 (1992).

Gwiazda, Jane, "Treatment Options for Myopia," retrieved from https://www.ncbi.nlm.nih.gov/pmc/articles/PMC2729053/, Optom Vis Sci., 86(6):624-628 (Jun. 2009).

Gwiazda, Jane, et al, "A Randomized Clinical Trial of Progressive Addition Lenses versus Single Vision Lenses on the Progression of Myopia in Children", Invest Ophthalmol Vis Sci, 44:1492-500 [PubMed: 12657584] (2003).

Haglund, Erik, et al., "Multi-wavelength VCSEL arrays using high-contrast gratings," Proc. of SPIE vol. 10113, 7 pages (2017).

Hammond, D.S., et al., "Dynamics of active emmetropisation in young chicks—influence of sign and magnitude of imposed defocus" Ophthalmic Physiol Opt. 33:215-222 (2013).

Henry W., "MicroLED Sources enable diverse ultra-low power applications", in Photonic Spectra, 2013.

International Search Report and Written Opinion for PCT/US2021/036100, 13 pages (dated Nov. 4, 2021).

Jayaraman, V., et al., "Recent Advances in MEMS-VCSELs for High Performance Structural and Functional SS-OCT Imaging," Proc. of SPIE vol. 8934, retrieved from http://proceedings.spiedigitallibrary.org/ on Dec. 1, 2015 (2014).

Jones, D., "Measure Axial Length to Guide Myopia Management," Review of Myopia Management, 5 pages (Apr. 9, 2020).

Kur, Joanna, et al., "Light adaptation does not prevent early retinal abnormalities in diabetic rats," Scientific Reports, 8 pages (Feb. 8, 2016).

Lagreze, Wolf A., et al., "Preventing Myopia," retrieved from https://www.ncbi.nlm.nih.gov/pmc/articles/PMC5615392/, Dtsch Arztebl Int., 114(35-36):575-580 (Sep. 2017).

Lam, Carly Siu Yin, et al., "Defocus Incorporated Multiple Segments (DIMS) spectacle lenses slow myopia progression: a 2-year randomised clinical trial," Br. J. Ophthalmol. 0:1-6 (2019).

Leo, Seo-Wei, et al., "An evidence-based update on myopia and interventions to retard its progression," J AAPOS, 15(2):181-189 (Apr. 2011).

Lingley, A.R., et al, : A single pixel wireless contact lens display, in J Micromech. Microeng., 2011; 21, 125014; doi:10.1088/0960-1317/21/12/125014, Abstract Only.

Martin, J.A., et al., "Predicting and Assessing Visual Performance with Multizone Bifocal Contact Lenses," Optom Vis Sci, 80(12):812-819 (2003).

Matkovic, K., et al., "Global Contrast Factor—a New Approach to Image Contrast," Computational Aesthetics in Graphics, Visualization and Imaging, 9 pages (2005).

McKeague C, et al. "Low-level night-time light therapy for age-related macular degeneration (ALight): study protocol for a randomized controlled trial", in Trials 2014, 15:246, http://www.trialsjournal.com/content/15/1/246.

(56) References Cited

OTHER PUBLICATIONS

Moreno, I, "Creating a desired lighting pattern with an LED array" in Aug. 2008, Proceedings of SPIE—The International Society for Optical Engineering 7058, DOI: 10.1117/12.795673.

Moreno, I., "Modeling the radiation pattern of LEDS", in Optics Express, 2008; 16, 3 pp. 1808.

Nickla, Debora L., et al., "Brief hyperopic defocus or form deprivation have varying effects on eye growth and ocular rhythms depending on the time-of-day of exposure," Exp Eye Res. 161:132-142 (Aug. 2017).

Ramsey, DJ, and Arden, GB, "Hypoxia and dark adaptation in diabetic retinopathy: Interactions, consequences and therapy", in Microvascular Complications—Retinopathy (JK Sun, ed.), Cur Dab Rep (2015) 15: 118, DOI 10.1007/s11892-015-0686-2, Abstract Only.

Read, Scott A., et al., "Choroidal changes in human myopia: insights from optical coherence tomography imaging," Clin Exp Optom, 16 pages (2018).

Read, Scott A., et al., "Human Optical Axial Length and Defocus," IOVS, 51(12):6262-6269 (2010).

Shivaprasad, S, et al, "Clinical efficacy and safety of a light mask for prevention of dark adaptation in treating and preventing progression of early diabetic macular oedema at 24 months (CLEOPATRA): a multicentre, phase 3, randomised controlled trial," in www.thelancet.com/diabetes-endocrinology vol. 6, pp. 382-391 (May 2018).

Smith, III, Earl L., "Optical treatment strategies to slow myopia progression: Effects of the visual extent of the optical treatment zone," retrieved from https://www.ncbi.nlm.nih.gov/pmc/articles/PMC3624048/, Exp Eye Res., 114:77-88 (Sep. 2013).

Srinivasan, S., "Ocular axes and angles: Time for better understanding," J. Cataract Refract. Surg., 42:351-352 (Mar. 2016).

Torii, Hidemasa, et al., "Violet Light Exposure Can Be a Preventive Strategy Against Myopia Progression," EBioMedicine 15:210-219 (2017).

U.S. Appl. No. 17/302,479, filed May 4, 2021 (60 pages).

Wallman, Josh, et al., "Homeostasis of Eye Growth and the Question of Myopia," Neuron, 43:447-468 (2004).

Wolffsohn, James A., et al., "Impact of Soft Contact Lens Edge Design and Midperipheral Lens Shape on the Epithelium and Its Indentation With Lens Mobility," IOVS, 54(9):6190-6196 (2013).

\* cited by examiner

Image contrast > Histrogram with RGB values

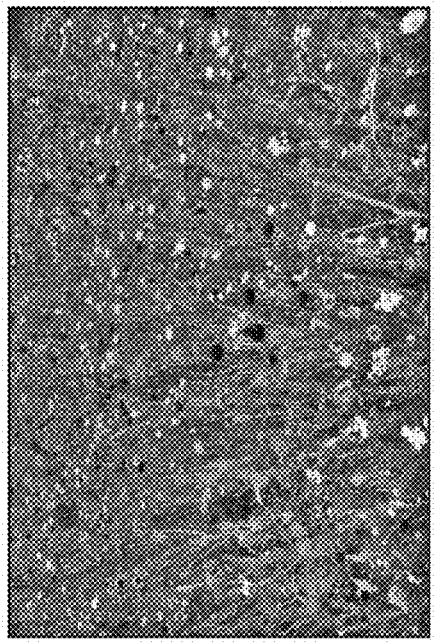
FIG. 12
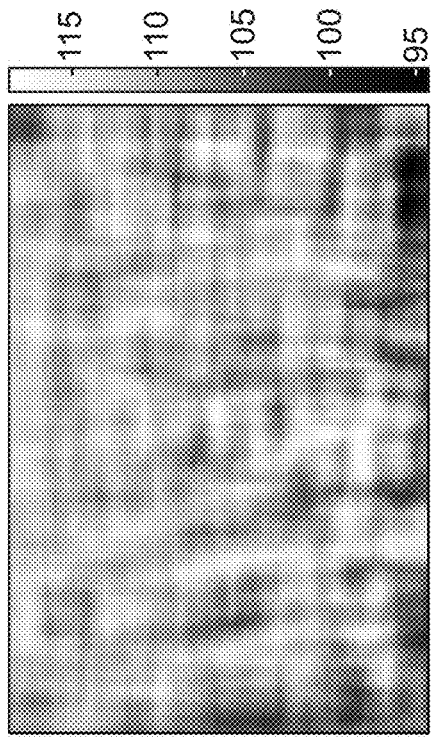
FIG. 14
FIG. 11
FIG. 13

PROJECTION OF DEFOCUSED IMAGES ON THE PERIPHERAL RETINA TO TREAT REFRACTIVE ERROR

RELATED APPLICATIONS

This application is a continuation of U.S. patent application Ser. No. 17/304,691, filed Jun. 24, 2021, now U.S. Pat. No. 11,275,259, issued Mar. 15, 2022, which is a continuation of International Application No. PCT/US2021/036100, filed Jun. 7, 2021, which published as WO 2021/252319 on Dec. 16, 2021, which claims priority to U.S. Provisional Patent Application No. 63/036,226, filed Jun. 8, 2020, to U.S. Provisional Patent Application No. 62/706,153, filed Aug. 3, 2020, and to U.S. Provisional Patent Application No. 62/706,456, filed Aug. 18, 2020, the entire disclosures of which are incorporated herein by reference.

The subject matter of the present application is related to PCT/US2019/043692, filed on Jul. 26, 2019, published as WO 2020/028177 A1 on Feb. 6, 2020, the entire disclosures of which is incorporated herein by reference.

BACKGROUND

Prior approaches to treating refractive error such as myopia can be less than ideal in at least some respects. Spectacle lenses, contact lenses, and refractive surgery can be used to treat refractive errors of the eye. However, lenses must be worn in order to correct the errors, and uncorrected refractive error can impact a person's ability to achieve and fully participate in school, sports, and other activities. Although surgery can be performed to decrease refractive error, surgery comes with risks, such as infection and degraded vision in at least some instances. Also, these approaches do not address the underlying changes in the length of the eye that is related to refractive error such as myopia.

Work in relation to the present disclosure suggests that the retina of many species, including human beings, responds to defocused images and is repositioned through scleral remodeling, in order to decrease the blur caused by the defocus. The mechanism of the generation of the growth signal is still under study, but one observable phenomenon is an increase in thickness of the choroid. A defocused image can cause the choroid thickness to change, which is related to the axial length of the eye. Changes to the axial length of the eye can alter the refractive error by changing the position of the retina in relation to the cornea. For example, an increase in axial length increases myopia of an eye by increasing the distance between the cornea and retina.

While the defocus of images can play a role in choroidal thickness and changes in the axial length of the eye, the prior approaches are less than ideally suited to address to refractive error of the eye related to axial length. Although pharmaceutical treatments have been proposed to treat myopia associated with axial length growth, these treatments can have less than ideal results and have not been shown to safely treat refractive error in at least some instances. Although light has been proposed as a stimulus to alter the growth of the eye, at least some of the prior devices can provide less than ideal results. Also, the time of treatment can be longer than would be ideal, and at least some of the prior approaches may be more complex than would be ideal.

Therefore, new approaches are needed to treat refractive error of the eye that ameliorate at least some of the above limitations of the prior approaches.

SUMMARY

The presently disclosed methods, devices and apparatus provide improved treatment of refractive error with decreased treatment times. In some embodiments, the stimulus comprises one or more of a spatial frequency distribution or a ratio of stimulus intensity to background illumination intensity to promote an improved response. In some embodiments, the stimulus is presented at an appropriate time of day to promote the response.

An apparatus to treat refractive error of the eye comprises one or more optics configured to project stimuli comprising out of focus images onto the peripheral retina outside the macula. While the stimuli can be configured in many ways, in some embodiments the stimuli are arranged to decrease interference with central vison such as macular vision. The stimuli can be out of focus images may comprise an amount of defocus within a range from about 2 Diopters ("D") to about 6 D, and the range can be from about 3 D to about 6 D. In some embodiments, the brightness of the stimuli is greater than a brightness of background illumination by an appropriate amount such as at least 3 times the background brightness. In some embodiments, each of a plurality of stimuli comprises a spatial frequency distribution with an amplitude profile having substantial spatial frequencies within a range from about range of $1\times10^{-1}$ to $1\times10^{1}$ cycles per degree. In some embodiments, each of the stimuli is sized and shaped with an intensity profile distribution so as to provide spatial frequencies to promote a response to the stimuli. Each of the stimuli may comprise one or more localized intensity peaks in proximity to a region of decreased illumination. In some embodiments, the region of deceased illumination is located between a plurality of peaks, although the region of decreased illumination may be bounded by an annular peak.

INCORPORATION BY REFERENCE

All patents, applications, and publications referred to and identified herein are hereby incorporated by reference in their entirety and shall be considered fully incorporated by reference even though referred to elsewhere in the application.

BRIEF DESCRIPTION OF THE DRAWINGS

A better understanding of the features, advantages and principles of the present disclosure will be obtained by reference to the following detailed description that sets forth illustrative embodiments, and the accompanying drawings of which:

FIG. 11 shows an image suitable for modification and incorporation as a stimulus as described herein, in accordance with some embodiments;

FIG. 12 shows an image similar to the image of FIG. 11 that has been processed to provide an improved stimulus, in accordance with some embodiments;

FIG. 13 shows an image of spatial frequencies distributions of the image of FIG. 11, in accordance with some embodiments;

FIG. 14 shows an image of spatial frequencies distributions of the image of FIG. 13, which is used as the stimulus, in accordance with some embodiments;

DETAILED DESCRIPTION

The following detailed description provides a better understanding of the features and advantages of the inventions described in the present disclosure in accordance with the embodiments disclosed herein. Although the detailed description includes many specific embodiments, these are provided by way of example only and should not be construed as limiting the scope of the inventions disclosed herein.

The presently disclosed methods and apparatus can be configured in many ways to provide retinal stimulation as described herein. The presently disclosed methods and apparatus are well suited for combination with many prior devices, such as one or more of an ophthalmic device, a TV screen, a computer screen, a virtual reality ("VR") display, an augmented reality ("AR") display, a handheld device, a mobile computing device, a tablet computing device, a smart phone, a wearable device, a spectacle lens frame, a spectacle lens, a near eye display, a head-mounted display, a goggle, a contact lens, an implantable device, a corneal onlay, a corneal inlay, a corneal prosthesis, or an intraocular lens. Although specific reference is made to spectacles and contact lenses, the presently disclosed methods and apparatus are well suited for use with any of the aforementioned devices, and a person of ordinary skill in the art will readily appreciate how one or more of the presently disclosed components can be interchanged among devices, based on the teachings provided herein.

Figure 1A:
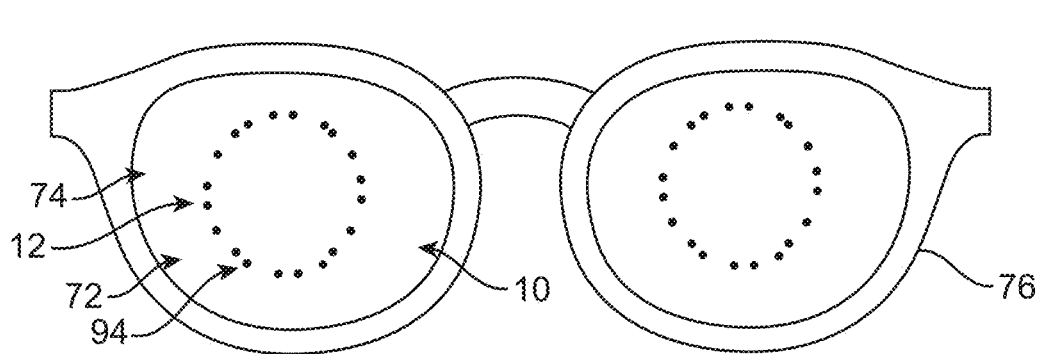
FIG. 1A shows a retinal stimulation device, in accordance with some embodiments.

FIG. 1A shows a retinal stimulation device to one or more of decrease myopia progression or at least partially reverse myopia progression. The device comprises a lens 10 to support a plurality of light sources. The plurality of light sources can be coupled to one or more optical components to provide a stimulus to the retina as described herein. In some embodiments, the lens 10 comprises a spectacle lens 74. In some embodiments, the lens 10 is shaped to correct spherical and cylindrical refractive errors of the user, to provide corrected visual acuity to through the lens. The plurality of light sources may comprise one or more of projection units 12 or a display 74 such as a near eye display. The plurality of light sources is arranged about the central portion of the lens so as to provide light stimulation to an outer location of the retina such as the peripheral retina as described herein. In some embodiments, the light sources are located in an approximately annular region so as to provide stimulation to the peripheral retina. The light sources can be arranged in a generally annular pattern, for example in quadrants, so as to correspond to quadrants of the peripheral retina outside the macula. Each of the plurality of light sources can be configured to project a pattern anterior to the retina with an appropriate stimulus pattern as described herein. In some embodiments, light from the light sources traverses an optical axis of the eye so as to stimulate the retina at a location on an opposite side of the retina from the light source.

In some embodiments, the projection units 12 are configured to emit light rays to enter the pupil of the eye without substantial aliasing. In some embodiments, the pupil of the eye may be enlarged by appropriate amounts of illumination or application of mydriatic agents so that a greater area of the retinal surface is accessible to the stimulus projected by the projection units 12.

In some embodiments, the plurality of light sources is configured to remain static while the user views an object. Alternatively, the light sources can be configured to move in response to eye movement, for example with the selective activation of pixels as described herein.

Although reference is made to the plurality of light sources supported on a lens, the light sources can be supported on any suitable optically transmissive substrate, such as a beam splitter or a substantially flat optical component, and the light sources may comprise light sources of a pixel display such as an AR or VR display. In some embodiments, the display 72 comprises pixels 94 which are selectively activated to provide a stimulus to the retina as described herein. Alternatively or in combination, the projection units 12 may comprise a shaped structure to provide the stimulus to the retina as described herein.

In some embodiments, the pixels are configured to emit a plurality of colors, so that the projected light can be combined to create any suitable color or hue, such as white light, for example.

In some embodiments, the plurality of light sources is supported a head mounted support, such as eyeglass frame 76 on spectacles 70.

Figure 1B:
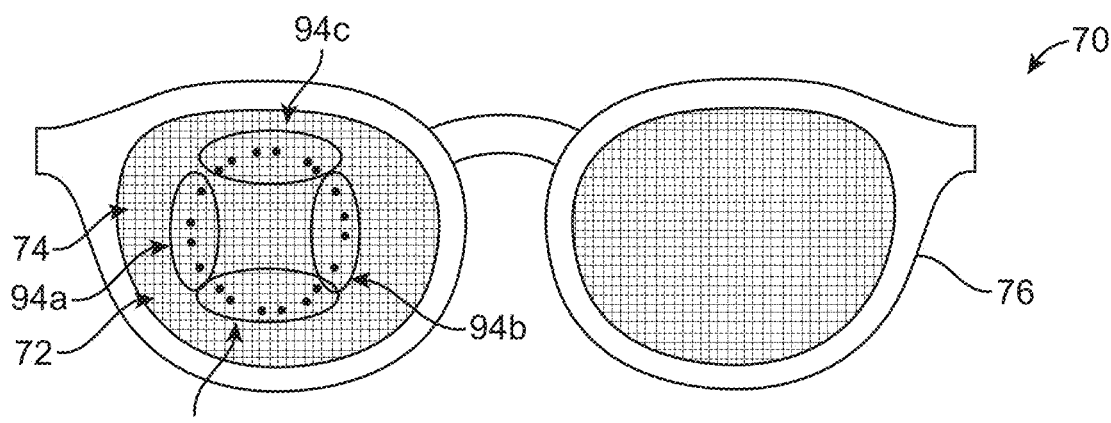
FIG. 1B shows a spectacle lens based retinal stimulation device comprising a display and a housing to contain the electronics for operating the near eye display, in accordance with some embodiments.
Figure 1C:
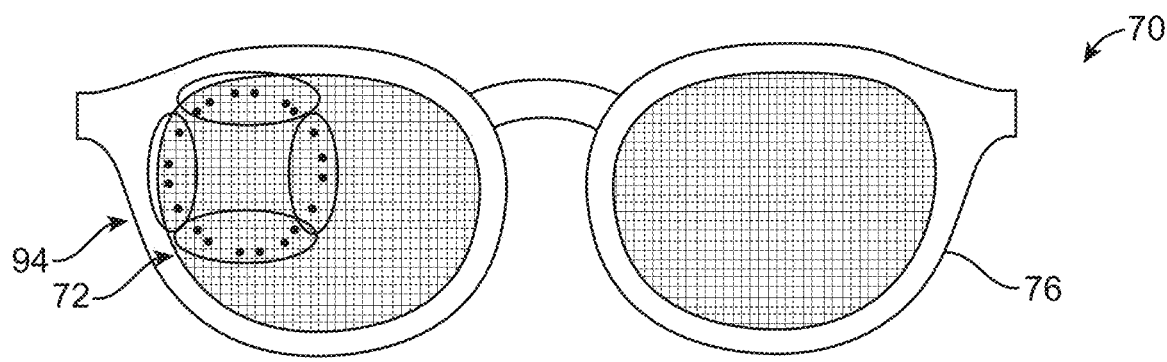
FIG. 1C shows a spectacle lens based retinal stimulation device as in FIG. 1B, in which the eye has moved and different display elements have been activated in response to the eye movement, in accordance with some embodiments.

FIGS. 1B and 1C depict spectacles 70 for the treatment of refractive error of the eye, such as spherical refractive error, although any suitable vision device as described herein can be appropriately modified in accordance with the embodiments disclosed herein. The plurality of light sources can be coupled to one or more optical components to provide a stimulus to the retina as described herein. The spectacles 70 may comprise one or more components of commercially available augmented reality glasses. The spectacle 70 may comprise one or more displays 72 for retina stimulation. The near eye displays 72 may be mounted to lenses 74. The lenses 74 may be spectacle lenses supported by eyeglass frame 76. The lens 74 may be a corrective or non-corrective lens. The lens 74 may be a plano lens, a spherical corrective lens, an astigmatic correction lens, or a prism correction lens. In some embodiments, the near eye display is located away from an optical zone to provide clear central vision. An optical axis may extend along a line of sight from an object of the patient's regard, though the lens 74 to a fovea of the eye. In some embodiments, the spectacle 70 comprises an eye tracker suitable for incorporation in accordance with the present disclosure. The near eye display 72 can be programmed to selectively activate pixels 94, in order to provide peripheral stimulation to the retina, as described herein. In some embodiments, a layer of a plastic substrate bearing micro-lenses is attached to the micro-display in order to generate the desired level of defocus and stimulation at the retina. The selectively activatable pixels may comprise a groups of pixels, which can be selectively activated together, e.g. a first group of pixels 94a, a second group of pixels 94B, a third group of pixels 94C, and a fourth group of pixels 94D. The groups of pixels can be arranged to provide an appropriate eccentricity with respect to a line of sight of the patient, so as to provide peripheral retinal stimulation as described herein.

In some embodiments, a near eye display 72 comprises a combination of a micro-display and a micro-optic. In some embodiments, the micro-optic is configured to collect, substantially collimate and focus the light rays emanating from the micro-display. In some embodiments, the micro-optic is configured to form an image anterior to or posterior to the retina as described herein. In some embodiments, the distance of the near eye display from the entrance pupil of the eye is within a range from about 10 mm to about 30 mm, for example about 15 mm. The micro-display can be placed on a transparent substrate, such as the front or back surface of the lens 74 of the spectacles 70. When the micro-display is placed on the front surface of the lens 94, then the focus of the micro-displays may be affected by the cylindrical correction on the back surface of the lens 94.

In some embodiments, the focus of the pixels in a micro-display may vary based on their location on the lens 74 and the refractive correction provided by the lens in that area. In some embodiments, the focus of the pixels may be fixed. In some embodiments, the focus of the pixels may vary based on the sensed position of the cornea to account for the refraction of the cornea and the lens of the eye. In some embodiments, the pixels are defocused to create a defocused spot on the retina about 1 mm in diameter.

Light emitted by the pixels 94 in the micro-display of the near eye display can be one or more of substantially collimated or focused before being directed to the pupil of the eye. In some embodiments, a micro-lens array is aligned to the pixels of the near eye display, so that rays from the near eye display can enter the pupil and form an image anterior to or posterior to the retina. In some embodiments, the width of the near eye display corresponds to a patient's field of view. In some embodiments, the extent of the near eye display may be substantially similar to the extent of the lens 74 of the spectacles 70.

In some embodiments, the device provides unimpaired central vision so that the quality of life and quality of vision of the users are not adversely affected. In some embodiments, central vision comprises of a field of view of +/−5 degrees or greater, preferably +/−7.5 degrees or greater, such as +/−12.5 degrees, covering the macula, while foveal vision used for fixation has a field of view of +/−1.0 degrees. In some embodiments, the defocused image is projected at an outer portion of the retina toward the periphery of the retina, for example within a range from 15 degrees (full angle, or +/−7.5 degrees) to 40 degrees (full angle, or +/−20 degrees) eccentric to the fovea and can be within a range from 20 degrees to 40 degrees, for example within a range from 20 degrees to 30 degrees. In some embodiments, the micro-display 72 does not obstruct the central vision field of view. In some embodiments, the pixels 94 do not obstruct the central vision field of view.

In some embodiments, the micro-displays and optics are configured to project light onto outer regions of the retina sufficiently far from the fovea, that the illumination remains substantially fixed even with eye movement. In some embodiments, the point of regard is monitored and the desired location of the pixels to be activated on the micro-display is determined, e.g. by a computations with a processor, such that an image is projected at the desired location on the retina, allowing sustained stimulation at the same retinal location. In some embodiments, the point of regard on the spectacle plane or the plane of the micro-display is calculated by monitoring the horizontal, the vertical and torsional displacement of the eye relative to the primary position.

The point of regard can be determined with a in many ways, for example with an eye position sensor such as a magnetic sensor or an optical sensor. In some embodiments, a search coil embedded in the eyeglass frame is used to track eye movements. The coil embedded in the eyeglass frame can be coupled to a magnetic structure placed on the eye, such as one or more of a coil on a contact lens, a coil implanted in the eye, a magnetic material on a contact lens, or a magnetic material implanted in the eye. In some embodiments, the sensor comprises an optical sensor, such as a position sensitive detector or an array sensor to measure a position of the eye optically. The optical sensor can be configured to measure a position of the eye in many ways, for example configured to measure a position of one or more of a corneal reflex from a light source, a pupil, a limbus or a sclera. The eyeglass frame may support an additional light source to illuminate the eye, for example to generate a corneal reflex. Data from the sensor can provide the location of the coaxially sighted corneal light reflex ("CSCLR"), and hence the direction of the visual axis and the location of the fovea. The point of regard, visual axis, optical axis, nodes of the eye, and CSCLR are described in "Ocular axes and angles: time for better understanding", Srinivasan, S., in J CATARACT REFRACT SURG—VOL 42, MARCH 2016. In some embodiments, the processor, using the eye position sensor, may be configured to adjust the optics, such as the pixels in the micro display to reduce movement of the stimulated locations of the retina in response to eye movement. In some embodiments, target locations of the peripheral images are computed from the location of the fovea based on the information form the eye position sensor and a real time ray tracing calculation provides the locations of the pixels to be activated in the micro-display. The time to selectively switch to a second plurality of pixels in response to the eye movement can be less than 100 milliseconds, for example less than 20 milliseconds.

In some embodiments, the location of the pixels in the micro-display to be activated to form the outer image toward the periphery of the retina is referenced from the optical center of the eyeglass optics, since it is the point of regard at primary gaze. In some embodiments, the location of the point of regard is calculated by taking into account eye movement relative to the position of the eye at primary gaze and calculating the location of the pixels to be activated with reference to the new point of regard. For example, FIG. 1B shows active pixels 94 when a patient is looking level and straight ahead, so-called primary gaze, while FIG. 1C shows active pixels 94 when a patient is looking up and to the left. In such a case, the shape of the array of pixels may be the same, but translated up and to the left, or the shape of the array may change.

In some embodiments, the device is binocular and comprises a micro-display and optics for each eye of the user. The micro-display can be optically coupled with one or more micro-optical components, designed to substantially collimate the illumination generated by the pixels of the micro-display and rendered convergent, before entering the pupil.

In some embodiments, a display 72 is mounted on the outer side of a spectacle lens and aligned with the spectacle lens optic such that the near eye display can provide a field of view of +/−40 degrees or greater, so that the micro-display can continue to provide peripheral retinal stimulus for the normal range of eye movements, typically +/−15 degrees laterally and +10 to −20 degrees vertically, including downgaze when reading or viewing near objects. In some embodiments, light from the micro-display is transmitted through the spectacle lens optic and provided with the refractive correction of the user.

In some embodiments, the optical system is configured to form the images anterior to the retina and comprises one or more of a single micro-lens (lenslet), a plurality of micro-lenses (lenslet array), a compound lens, such as a Gabor lens, a micro-prism, or a micro-mirror, or a combination thereof. In some embodiments, light baffles and micro-mirrors are arranged to ensure that the amount of light not captured by the micro-optic is substantially decreased, e.g. minimized, in order to reduce stray light and light escaping from the front side of the display.

In some embodiments, a pixel fill factor less than 10% (0.1) is sufficiently sparse to provide a clear view of the foveal and macular image. In some embodiments, the fill factor is in the range of 0.01 to 0.3 and can be within a range from 0.05 to 0.20. For example, an array of pixels of pixel size 5 microns and a pixel pitch of 20 microns leads to a fill factor of 0.06. A low fill factor may also reduce the complexity of the manufacturing process and reduces the cost of such micro-optic displays.

In some embodiments, the micro-optic array is designed to be optically aligned with the display, so that light from a single or a plurality of pixels 94 can be collected, collimated and focused to be directed to the pupil of the user at primary gaze. The density of these micro-optical elements can control the overall visibility of the near eye display. In some embodiments, the micro-optic has a low fill factor (preferably equal to or less than 0.1) so that the overall light transmission through the near eye display will be acceptable to users and allow the patient to view objects.

In some embodiments, the device comprises a switchable micro-optic array that can be switched between a plano (no optical power) state and an activated state by electro-optical components, utilizing for example a liquid crystal or a LC based material that can be switched from one refractive index to another, or one polarization to another, for example. In some embodiments, the micro-optic array does not scatter light or distort images of the real world when it is not activated.

In some embodiments, the location of the pixels in the micro-display to be activated to form the outer image toward the periphery of the retina is referenced from the optical center of the eyeglass optics, since it is the point of regard at primary gaze. In some embodiments, the location of the point of regard is calculated by taking into account eye movement relative to the position of the eye at primary gaze and calculating the location of the pixels to be activated with reference to the new point of regard.

In some embodiments, a plurality of pixels is activated to form the light source that is imaged by the micro-optics. The optical design of the micro-optics and its separation from the micro-display can be configured to provide the focal length of the image delivery system, the image magnification of the image projected on the retina and the blur caused by diffraction, as measured as the Airy disc diameter of the optical delivery system.

Work in relation to the present disclosure suggests that the retina perceives changes in image blur caused by higher order aberrations present in the defocused image (in addition to the spherical defocus), including longitudinal chromatic aberration (LCA), higher order spherical aberration, astigmatism, etc. that are sensitive to the sign of the defocus. Based on the teachings provided herein a person of ordinary skill in the art can conduct experiments to determine whether the retina can recognize a myopic blur from a hyperopic blur when the depth of focus of the device is greater than or nearly equal to the magnitude of defocus. The device as described herein can be appropriately configured to provide appropriate amounts of defocus at appropriate locations, for example.

The device can be configured to provide appropriate image magnification, diffraction that limits the image resolution and depth of focus in relation to the magnitude of myopic defocus being applied and the rate of change of image blur or image sharpness gradient as a function of the magnitude of defocus.

In some embodiments, the near eye display is configured to provide a clear, substantially undistorted field of view of the foveal and macular image for comfortable vision. In some embodiments, the field of view of the central image is at least +/−5 degrees and can be more (e.g. +/−12 degrees), for example, in order to account for differences in interpupillary distance (IPD) of different users, for example. Image quality and field of view of the real image can be provided with a substantially transparent near eye display transparent, and by reducing the fill factor of light emitting pixels in the micro-display. In some embodiments, a fill factor less than 10% (0.1) is sufficiently sparse to provide a clear view of the foveal and macular image. In some embodiments, the fill factor is in the range of 0.01 to 0.3 and can be within a range from 0.05 to 0.20. For example, an array of pixels of pixel size 5 microns and a pixel pitch of 20 microns will lead to a fill factor of 0.06. A low fill factor may also reduce the complexity of the manufacturing process and reduces the cost of such micro-optic displays.

In some embodiments, the micro-optic array is designed to be optically aligned with the display, so that light from a single or a plurality of pixels can be collected, collimated and focused to be directed to the pupil of the user at primary gaze. The population density of these micro-optical elements can control the overall visibility of the near eye display. In some embodiments, the micro-optic has a low fill factor (preferably equal to or less than 0.1) so that the overall light transmission through the near eye display will be acceptable to users.

In some embodiments the device comprises a switchable micro-optic array that can be switched between a plano (no optical power) state and an activated state by electro-optical components, utilizing for example a liquid crystal or a LC based material that can be switched from one refractive index to another, or one polarization to another, for example. In some embodiments, the micro-optic array does not scatter light or distort images of the real world when it is not activated.

Figure 2A:
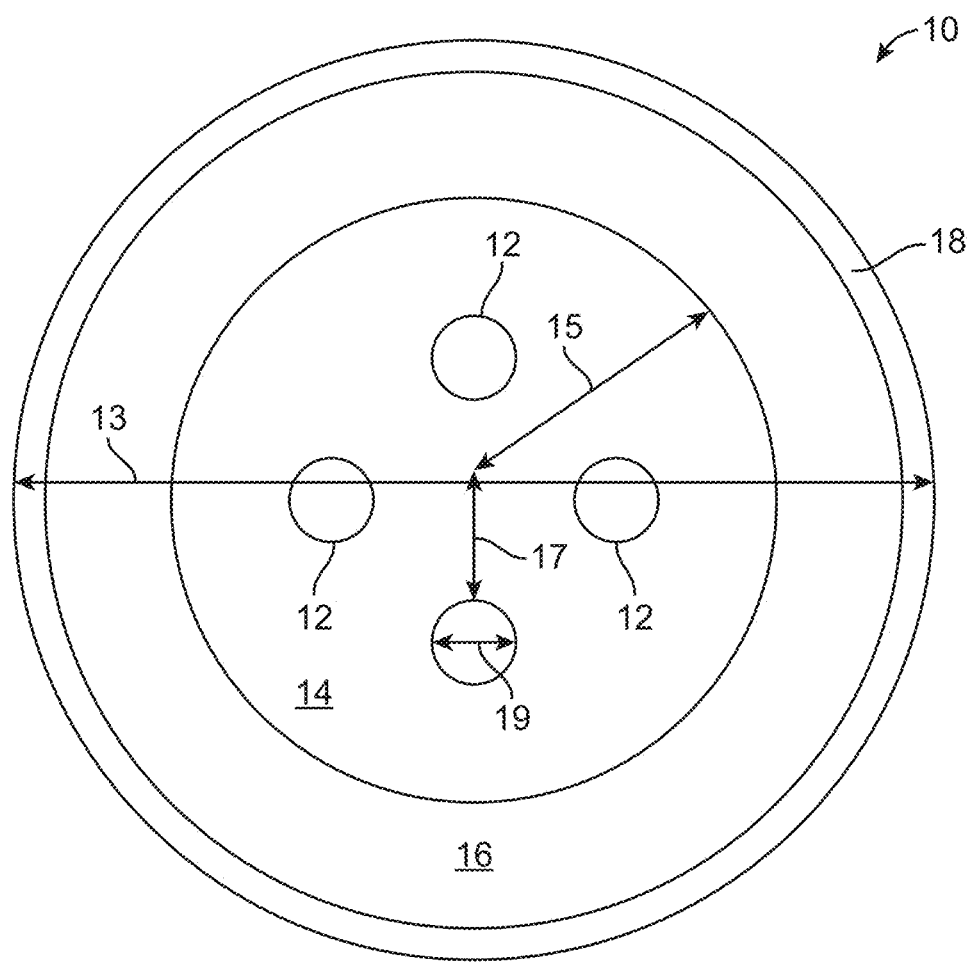
FIG. 2A shows a soft contact lens, in accordance with some embodiments.
Figure 2B:
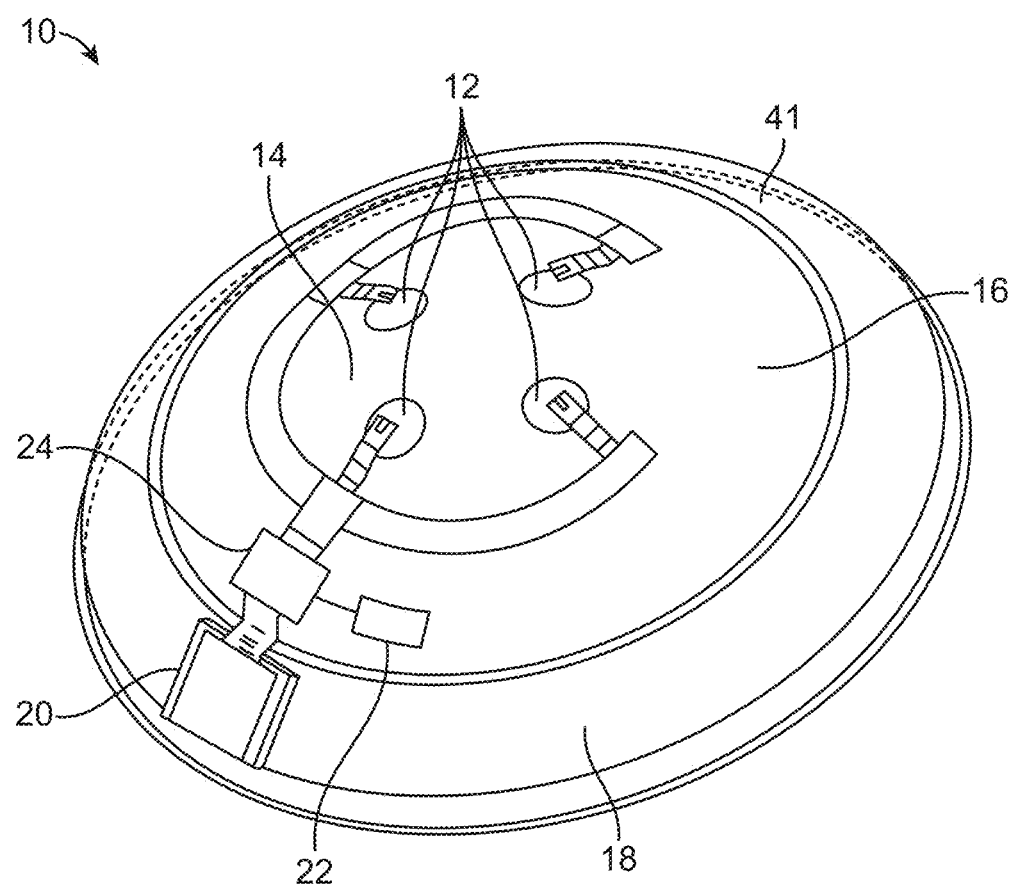
FIG. 2B shows soft contact lens with embedded light sources, optics and electronics for projecting images with defocus on the periphery of the retina of a user, in accordance with some embodiments.

FIGS. 2A and 2B depict a contact lens 10 comprising a plurality of light sources configured to project a defocused image on the retina away from the central field that includes the macula in order to stimulate a change in choroidal thickness. The plurality of light sources can be coupled to one or more optical components to provide a stimulus to the retina as described herein. Although reference is made to a contact lens, the lens 10 may comprise a lens of one or more of a projector, an ophthalmic equipment, a TV screen, a computer screen, an augmented realize display, a virtual reality display, a handheld device such as a smart phone, a wearable device such as a spectacle lens, a near eye display, a head-mounted display, a goggle, a contact lens, a corneal onlay, a corneal inlay, a corneal prosthesis, or an intraocular lens.

This contact lens 10 comprises a base or carrier contact lens comprising embedded electronics and optics. The base soft contact lens 10 is made of a biocompatible material such as a hydrogel or a silicone hydrogel polymer designed to be comfortable for sustained wear. The contact lens comprises a maximum overall distance across, e.g. a diameter 13. The biocompatible material can encapsulate the components of the soft contact lens 10. In some embodiments, the contact lens 10 has a central optical zone 14 designed to cover the pupil of a user's eye under many illumination conditions. In some embodiments, the optical zone comprises a circular zone defined with a radius 15. In some embodiments, a plurality of projection units 12 is located a distance 17 from a center of the optical zone. Each of the plurality of projection units 12 comprises a distance across 19. In some embodiments, the distances between the projection units are sized to place the projection units outside the optical zone to stimulate a peripheral region of the retina, although the projection units can also be placed inside the optical zone to stimulate the peripheral retina as described herein.

The optical zone 14 can be appropriately sized for the pupil of the eye and the illumination conditions during treatment. In some embodiments, the optical zone comprises a diameter of 6 mm, for example when the contact lens is configured for use during the day. The optical zone 14 may have a of diameter within a range from 6 mm to 9 mm, for example within a range from 7.0 mm to 8.0 mm. The central optical zone 14 is designed to provide emmetropic correction or other suitable correction to the user, and may be provided with both spherical and astigmatic correction. The central optical zone 14 is circumscribed by an outer annular zone, such as a peripheral zone 16 of width in a range 2.5 mm to 3.0 mm. The peripheral zone 16, sometimes referred to as the blend zone is primarily designed to provide a good fit to the cornea, including good centration and minimum decentration. The outer annular zone is surrounded by an outermost edge zone 18 of width in the range from 0.5 mm to1.0 mm. The optical zone 14 is configured to provide refractive correction and can be spherical, toric or multifocal in design, for example with a visual acuity of 20/20 or better. The outer annular zone peripheral to the optical zone 14 is configured to fit the corneal curvature and may comprise rotational stabilization zones for translational and rotational stability, while allowing movement of the contact lens 10 on the eye following blinks. The edge zone 18 may comprise a thickness within a range from 0.05 mm to 0.15 mm and may end in a wedge shape. The overall diameter 13 of the soft contact lens 10 can be within a range from 12.5 mm to 15.0 mm, for example within a range from 13.5 mm to 14.8 mm.

The contact lens 10 includes a plurality of embedded projection units 12. Each of the plurality of projection units 12 comprises a light source and one or more optics to focus light in front of the retina as described herein. Each of the optics may comprise one or more of a mirror, a plurality of mirrors, a lens, a plurality of lenses, a diffractive optic, a Fresnel lens, a light pipe or a wave guide. The contact lens 10 may comprise a battery 20 and a sensor 22. The contact lens 10 may comprise a flex printed circuit board (PCB) 24, and a processor can be mounted on the flex PCB 24. The processor can be mounted on the PCB 24 and coupled to the sensor 22 and the plurality of light sources 30. The soft contact lens 10 may also comprise wireless communication circuitry and one or more antennae 41 for electronic communication and for inductively charging the battery 20 of the contact lens 10. Although reference is made to a battery 20, the contact lens 10 may comprise any suitable energy storage device.

The projection units 12 can be configured to provide defocused images to the peripheral portion of the retina as described herein and may include light sources and projection optics. In some embodiments, one or more projection optics are configured with the light sources to project a defocused image from the light sources onto the peripheral retina away from the central visual field that includes the macula in order to stimulate a change in choroidal thickness, such as an increase or decrease in cordial thickness. The one or more projection units 12 can be configured to stimulate the retina without degrading central vision and corresponding images formed on one or more of the foveal or macular regions of the retina. In some embodiments, the one or more projection optics do not decrease the image forming characteristics of the vision correction optics prescribed to correct refractive errors of the users. This configuration can allow the user to have good visual acuity while receiving therapy from the defocused images as described herein.

In some embodiments, the light from light sources of the projection units 12 are substantially collimated and focused by one or more projection optics, as described herein. The function of the light sources and the projection optics is to substantially collimate the light emitted by the light sources and direct it at a focus that is designed to be in the front of or behind the retina to provide appropriate defocus to stimulate a change in choroidal thickness. For myopic defocus, the focused images may appear approximately 1.5 mm to 2.5 mm in front of the peripheral retina and myopic by about 2.0 D to 5.0 D, for example 2.0 D to 4.0 D, or preferably 2.5 D to 3.5 D, for example. For hyperopic defocus, he focused images may appear approximately 1.5 mm to 2.5 mm behind of the peripheral retina, in order to be hyperopic by about −2.0 D to −5.0 D, for example −2.0 D to −4.0 D, or preferably −2.5 D to −3.5 D, for example.

The plurality of stimuli and the clear zone can be arranged to allow eye movements relative to the projection optics and clear zone, which can be well suited for use in embodiments where the eye moves relative to the projection optics, such as spectacle, AR and VR applications. In accordance with some embodiments, light from the projection units may be directed at an oblique angle with respect to an optical axis of the eye in order to enter the pupil while maintaining a clear central vision zone that is substantially larger than the pupil in order to provide a large field of view of the clear zone, e.g. a large eye box. The clear zone can be dimensioned in many ways, and may comprise a circular zone, an oval, a square zone or a rectangular zone. In some embodiments, the eye box may be 5.0 mm by 4.0 mm. In some embodiments, the clear zone comprises an eye box may be 15 mm by 4.0 mm. A larger clear viewing zone, e.g. a larger eye box, allows a greater level of eye movements without the stimulus being blocked by the edge of the pupil, for example when the eye changes direction in gaze and the clear viewing zone defined by the eye box remains stationary. In some embodiments, the oblique angle of projection of the stimulus into the eye depends upon the size of the eye box.

In accordance with some embodiments, the lens 10 or other suitable optical support structure comprises projection units which include projection optics and micro-displays as the light source. The micro-displays may comprise an OLED (organic light emitting diode) or an array of micro-LEDs. Light emitted by these displays may be Lambertian. In some embodiments, the micro-display is optically coupled to a micro-optical array that substantially collimates and focuses the light emanating from the micro-display. The micro-display may comprise one or more miniaturized pixels. In some embodiments, the micro-display forms an extended array of pixels, characterized by a pixel size and a pixel pitch, in which the pixel size and the pixel pitch together correspond to a fill factor of the micro-display. As described herein, each of the pixels may have a size within a range from about 2 microns to about 100 microns, and the pixel pitch may range from 10 microns to 1.0 mm, for example. The corresponding fill factor can range from 0.1% to 10% or more. In some embodiments where real world viewing is desirable, a smaller fill factor blocks less light from the real environment and provides a greater level of comfort and vision. Alternatively or in combination, a greater fill factor can enhance the overall brightness of the stimulus and may be well suited for applications that do not rely on real word viewing and all around vision. In some embodiments, the pixel array is optically coupled with a micro-optic array in order to substantially collimate and focus light from the pixels.

In accordance with some embodiments, the lens 10 or other suitable optical support structure comprises projection units which include projection optics and micro-displays as the light source. The micro-displays may comprise an OLED (organic light emitting diode) or an array of micro-LEDs. Light emitted by these displays may be Lambertian. In some embodiments, the micro-display is optically coupled to a micro-optical array that substantially collimates and focuses the light emanating from the micro-display. The micro-display may comprise one or more miniaturized pixels. In some embodiments, the micro-display forms an extended array of pixels, characterized by a pixel size and a pixel pitch, in which the pixel size and the pixel pitch together correspond to a fill factor of the micro-display. As described herein, each of the pixels may have a size within a range from about 2 microns to about 100 microns, and the pixel pitch may range from 10 microns to 1.0 mm, for example. The corresponding fill factor can range from 0.1% to 10%. In some embodiments, the pixel array is optically coupled with a micro-optic array in order to substantially collimate and focus light from the pixels.

The images created by these displays is defocused and may be placed symmetrically in four quadrants of the field of view or of the eye (e.g. nasal-inferior, nasal-superior, temporal-inferior and temporal-superior). The micro displays can be located away from the optical center of the lens by a distance within a range from 1.5 mm to 4.0 mm, preferably 2.5 mm to 3.5 mm. The central optic of the contact lens can be selected to bring the user to emmetropia, and may have a diameter within a range 3.0 to 5.0 mm. Each micro-display may be circular, rectangular or arcuate in shape and have an area within a range from 0.01 mm2 to 8.0 mm2, for example within a range from 0.04 mm2 to 8.0 mm2, for example within a range from 1 mm2 to 8 mm2, or preferably within a range from 1.0 mm2 to 4.0 mm2, in some embodiments.

The micro-display can be coupled to and supported with the body of the correction optic such as a contact lens, or a spectacle lens, an augmented reality ("AR") headset, or a virtual reality ("VR") headset for example. In some embodiments, the micro-displays are coupled to and supported with one or more of an intraocular lens, a corneal prosthesis, a corneal onlay, or a corneal inlay. The optical configurations described herein with reference to a contact lens can be similarly used with one or more of an intraocular lens, a corneal prosthesis, a corneal onlay, or a corneal inlay, for example.

In some embodiments, the micro-displays and the micro-optic arrays are mounted immediately adjacent to each other on the same correction optic, separated by a fixed distance in order to project a bundle of rays to the pupil of the eye, at an orientation that it forms a defocused image at a desired location on the retina as described herein. In some embodiments, the one or more projection optics are mounted on or in the one or more correction optics, such that rays from the projection optics are refracted through the correction optics. The correction optics refract the rays from the projection optics to be convergent or divergent as helpful for clear vision, so that the micro-optical array can provide the desired magnitude of additional power that may be plus or minus, depending on the magnitude and sign of the defocus desired. The micro-display may be monochromatic or polychromatic, for example.

In some embodiments, the projected defocused image can be provided by a micro-display comprising a screen comprising one or more of an LCD screen, a screen driven by OLEDS (organic light emitting diodes), TOLEDS, AMO-LEDS, PMOLEDS, or QLEDS.

Figure 3:
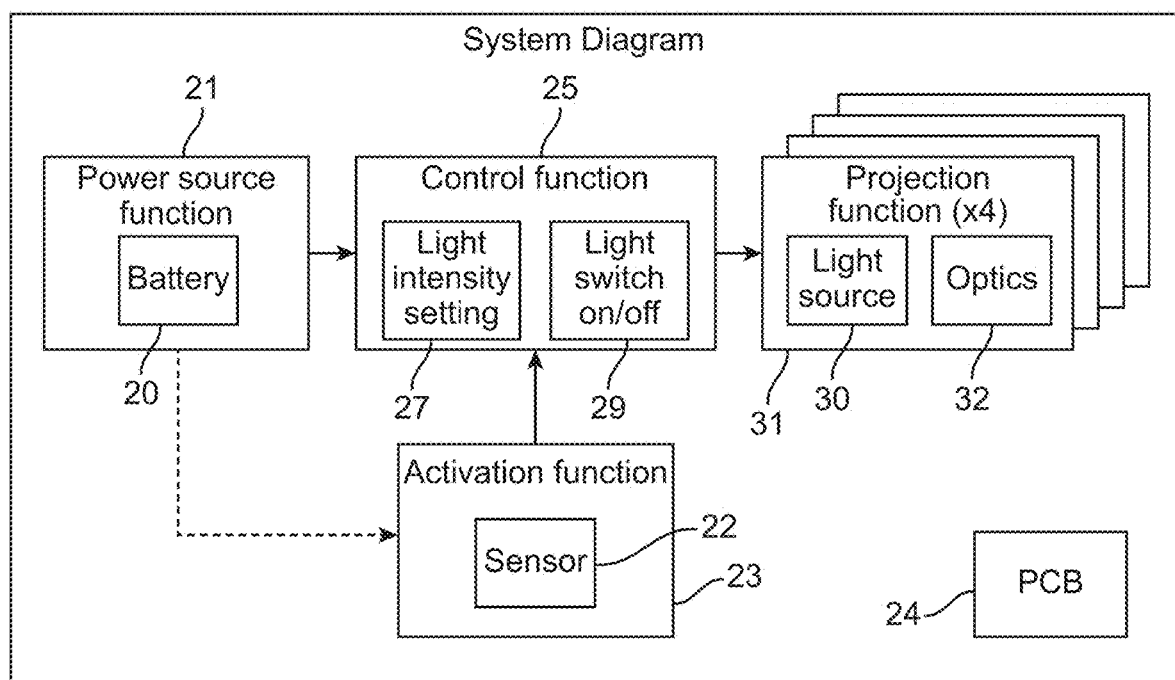
FIG. 3 shows a system diagram of the function of the components of the contact lens as in FIG. 2.

FIG. 3 shows system diagram of the function of the components of a retinal stimulation device, such as a lens 10 as in FIGS. 1A to 2B. These components can be supported with the PCB 24. For example, the power source, such as a battery 20, can be mounted on the PCB 24 and coupled to other components to provide a power source function 21. The sensor 22 can be configured to provide an activation function 23. The sensor 22 can be coupled to a processor mounted on the PCB 24 to provide a control function 25 of the lens 10. The control function 25 may comprise a light intensity setting 27 and a light switch 29. The processor can be configured to detect signal from the sensor 22 corresponding to an increase in intensity, a decrease in intensity, or an on/off signal from the sensor 22, for example with a coded sequence of signals from the sensor 22. The processor is coupled to the light projection units 18 which can comprise a light source 30 and optics 32 to provide the projection function 31. For example, the processor can be coupled to the plurality of light sources 30 (e.g. projection units 12 or one or more displays 72) to control each of the light sources 30 in response to user input to the sensor 22.

The retinal stimulation device may comprise global positioning system (GPS) circuitry for determining the location of the user, and an accelerometer to measure body movement, such as head movement. The retinal stimulation device may comprise a processor coupled to one or more of the GPS or the accelerometer to receive and store measured data. In some embodiments, the GPS along with a local clock (clock keeping local time) are used by a processor to compute the occurrence of diurnal variations in axial length of the eye of the wearer. In some embodiments, application of the stimulus may be made to coincide with the occurrence of maximum axial length under diurnal variations. The retinal stimulation device may comprise communication circuitry, such as wireless communication circuitry, e.g. BLUETOOTH® or WIFI, or wired communication circuitry, e.g. a USB, in order to transmit data from the device to a remote server, such as a cloud-based data storage system. This transmission of data to the remote server can allow the treatment and compliance of the user to be monitored remotely. In some embodiments, the processor comprises a graphics processing unit (GPU). The GPU can be used to efficiently and rapidly process content from the web in order to utilize this content in forming the stimulus as described herein.

The methods and apparatus for retinal stimulation as described herein can be configured in many ways and may comprise one or more attributes to encourage a user to receive therapy. For example, the retinal stimulation as described herein can be combined with a display of a game to encourage a user to wear the treatment device. In some embodiments, the retinal stimulation can be combined with another stimulus, such as an emoji, to encourage a user to wear the device for treatment. The components of the system may communicate with or receive information from a game or other stimulus to facilitate the retinal stimulation with the game or stimulus.

Figure 4A:
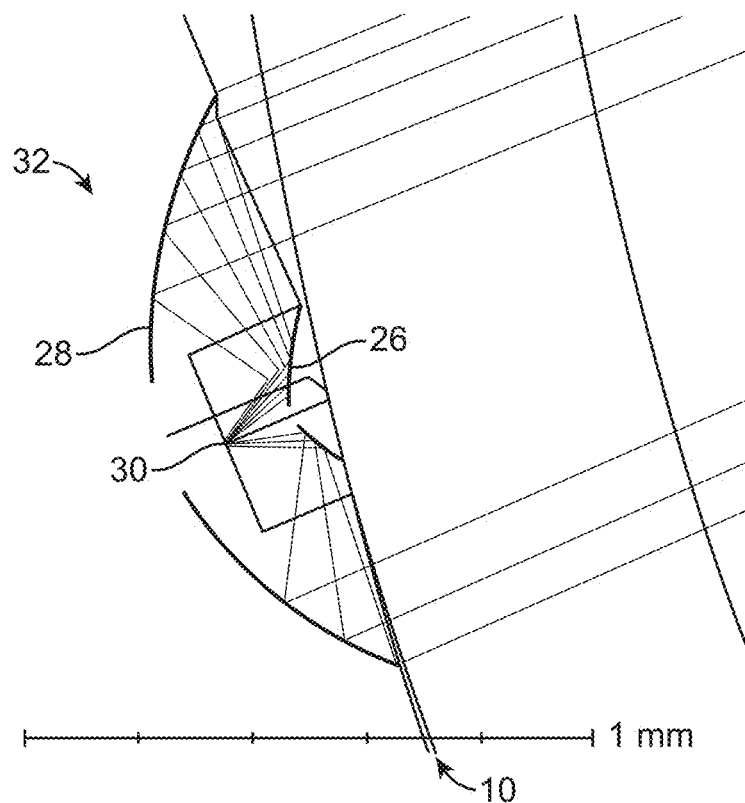
FIG. 4A shows an optical configuration in which the optical path length is increased by folding the optical path with two mirrors, in accordance with some embodiments.
Figure 4B:
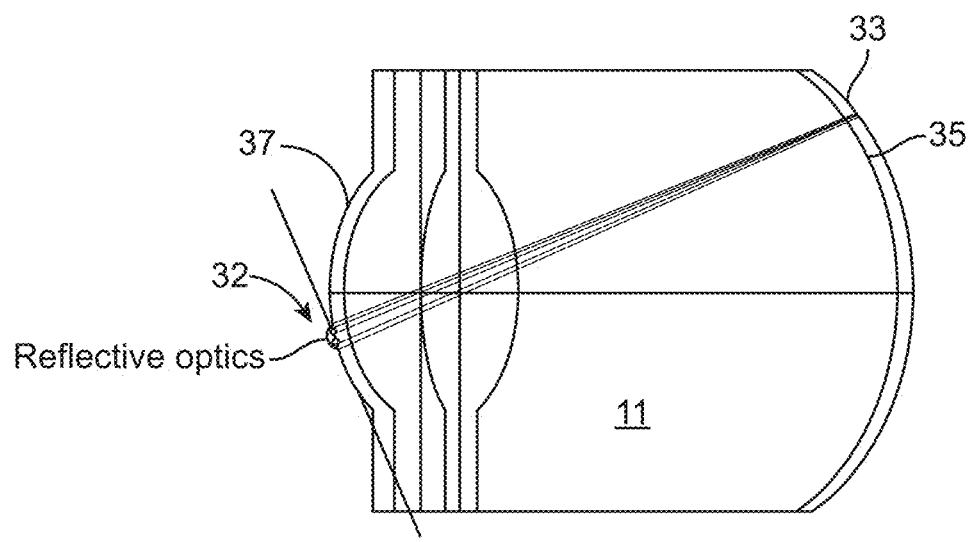
FIG. 4B shows the optical configuration as in FIG. 4A projecting light into an eye, in accordance with some embodiments.

Referring to FIG. 4A, the optic configuration 32 comprises a plurality of mirrors configured to collect light emitted by the micro-displays, then direct the light beam to the pupil of the eye 11, in order to form an eccentric retinal image, as shown in FIG. 4B. The mirrors may substantially collimate the light beam or direct the light beam toward the retina 33 with a suitable vergence so as to focus the light beam onto the retina 33.

Although the optic configurations shown in FIGS. 4A and 4B refer to a lens, such as a contact lens, a similar optical configuration can be used with a lens of one or more of a projector, an ophthalmic equipment, a TV screen, a computer screen, a handheld device such as a smart phone, a wearable device such as a spectacle lens, a near eye display, a head-mounted display, a display mounted on a helmet, an AR display, a VR display, a goggle, a contact lens, a corneal onlay, a corneal inlay, a corneal prosthesis, or an intraocular lens. Also, although reference is made to a myopic defocus, the defocus may comprise a hyperopic defocus, an astigmatic defocus, or an image focused onto the retina, or other defocus for the correction of refractive error as described herein, for example.

The mirror assembly shown in FIG. 4A can be configured to achieve a depth of focus that is less than 1 D, enabling the applied defocus of 2.0-4.0 D to be clearly perceived by the peripheral retina 33 at the specified radial eccentricity (e.g. within a range from 5 degrees to 30 degrees, or from 20 degrees to 30 degrees).

Figure 5A:
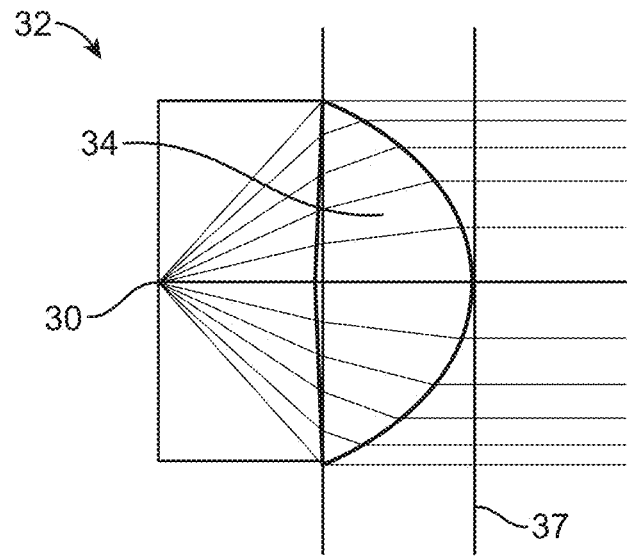
FIG. 5A shows an optical configuration comprising a lens to focus light onto the retina, in accordance with some embodiments
Figure 5B:
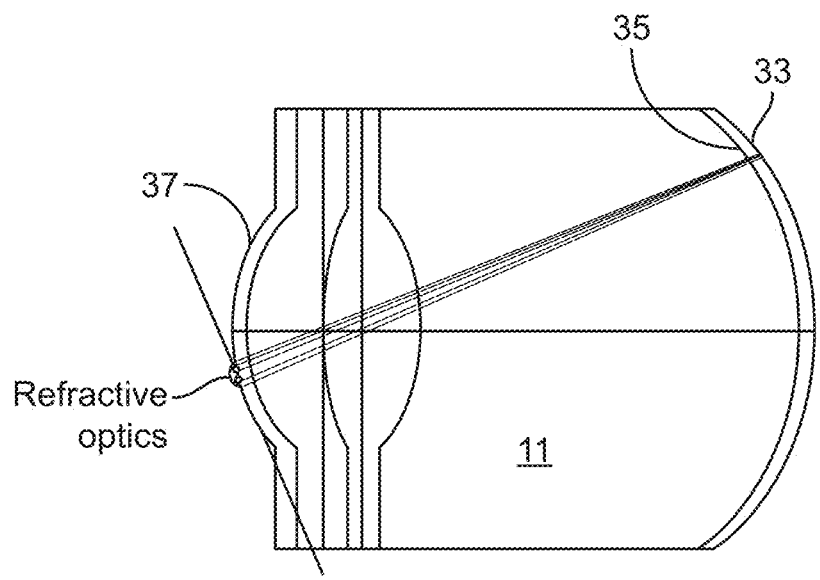
FIG. 5B shows an optical configuration as in FIG. 5A projecting light into an eye, in accordance with some embodiments.

As shown in FIGS. 5A and 5B, another embodiment comprises optics 32 comprising a converging or collimating lens in optical coupling with light source 30. In this configuration a lens 34, which may comprise a single lens, is used to substantially collimate the light output from the stimulation source and direct it to the cornea 37 through the lens such as contact lens 10. Although reference is made to a contact lens, the lens may comprise a lens of one or more of a projector, an ophthalmic equipment, a TV screen, a computer screen, a handheld device such as a smart phone, a wearable device such as a spectacle lens, a near eye display, a head-mounted display, a VR display, and AR display a goggle, a contact lens, a corneal onlay, a corneal inlay, a corneal prosthesis, or an intraocular lens.

The effectiveness of the collimating lens 34 depends on its refractive index and should be sufficiently high in order to create a substantial difference in refractive indices between the lens material and the material of the contact lens 10 that functions as the substrate. In this example, the refractive index of the embedded lens 34 has been assumed to be 2.02 (e.g., refractive index of a lanthanum fluorosilicate glass LaSF5), although other materials may be used.

Figure 6A:
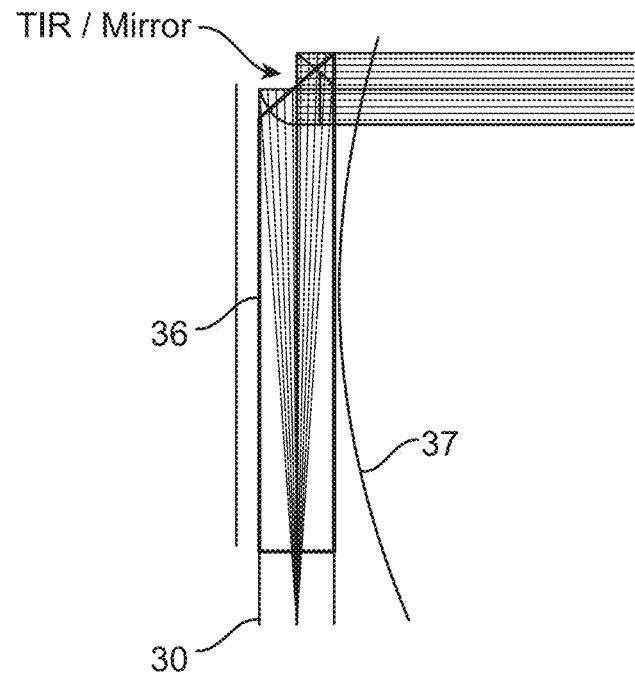
FIG. 6A shows a light-pipe in order to increase the optical path length, in accordance with some embodiments.
Figure 6B:
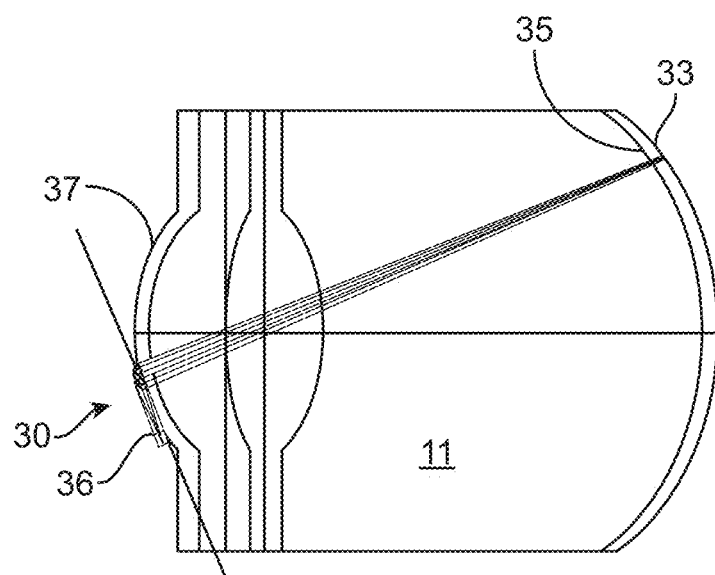
FIG. 6B shows an optical configuration as in FIG. 6A projecting light into an eye, in accordance with some embodiments.

Another embodiment comprises a light-pipe 36 in order to increase the optical path length, as shown in FIGS. 6A and 6B. The light-pipe 36 can provide an increased optical path length to provide appropriate image magnification, for example from 0.5× to 8× magnification, preferably from 1× to 3× magnification, and retinal image size.

Although reference is made to a light pipe 36 on a cornea 37 as would occur with a contact lens, the lens combined with the light pipe 36 may comprise a lens of one or more of a projector, an ophthalmic equipment, a TV screen, a computer screen, a handheld device such as a smart phone, a wearable device such as a spectacle lens, a near eye display, a head-mounted display, a VR display, an AR display, a goggle, a contact lens, a corneal onlay, a corneal inlay, a corneal prosthesis, or an intraocular lens.

Numerous other optical configurations may be used, including the use of a micro-lens array with a point source, use of diffractive optics in order to use a thinner lens, generation of multiple retinal images using a single point source and an optical processing unit.

Figure 7:
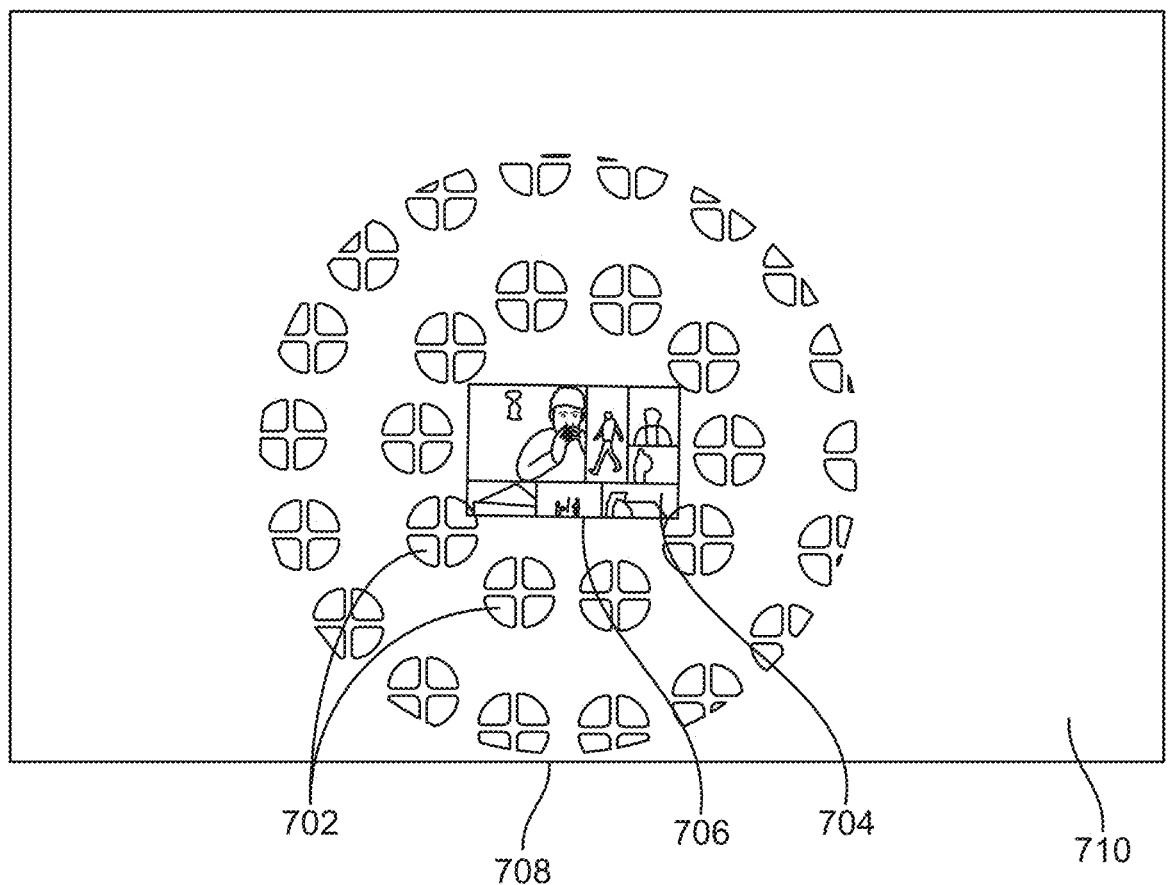
FIG. 7 shows a plurality of stimuli and an image on a display as seen by a user, in accordance with some embodiments.

FIG. 7 shows a plurality of stimuli 702 and an image 704 on a display 706 as seen by a user. The stimuli 702 are located around a display 706, in which the display corresponds to a region of clear central vision, and the stimuli correspond to peripheral vision of the user, for example vision outside the macula. The plurality of stimuli can be imaged anterior to the retina with a myopic defocus, so as to provide a stimulus to increase choroidal thickness and decrease growth in the axial length of the eye.

The stimuli can be configured in many ways as described herein. In some embodiments, the stimuli comprise a light pattern 708 on a dark background 710, e.g. a black and white pattern. In some embodiments, the stimuli comprise a polychromatic pattern on a darker background, such as a white or nearly white stimulus on a gray background or substantially black background. In some embodiments, each of the stimuli comprises a dark inner region and one or more light outer regions on a dark background, e.g. a dark cross through a white circular region a dark background. Stimuli may be selected based on their global contrast factor, their polarity (e.g., white or polychromatic on black background, versus, black on white or polychromatic background). The stimuli can be configured in many ways and may comprise a plurality of repeated icons shown on a display. The stimuli may be arranged in a circular or annular pattern of repeated icons. The stimuli may comprise any suitable global contrast factor, such as a global contrast factor of at least 0.5, at least 0.7, or at least 0.8, for example.

Figure 8B:
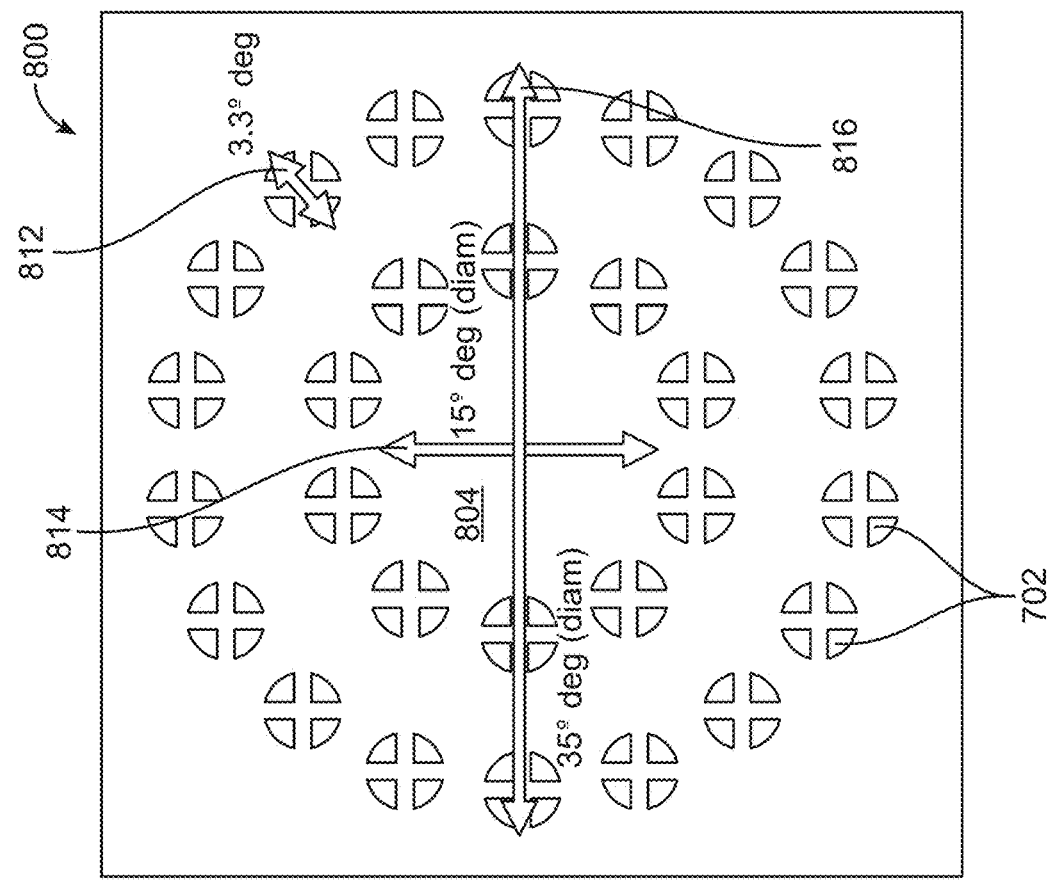
FIG. 8B shows the corresponding dimensions of the myopically defocused stimuli on the retina in degrees, in accordance with some embodiments.
Figure 8A:
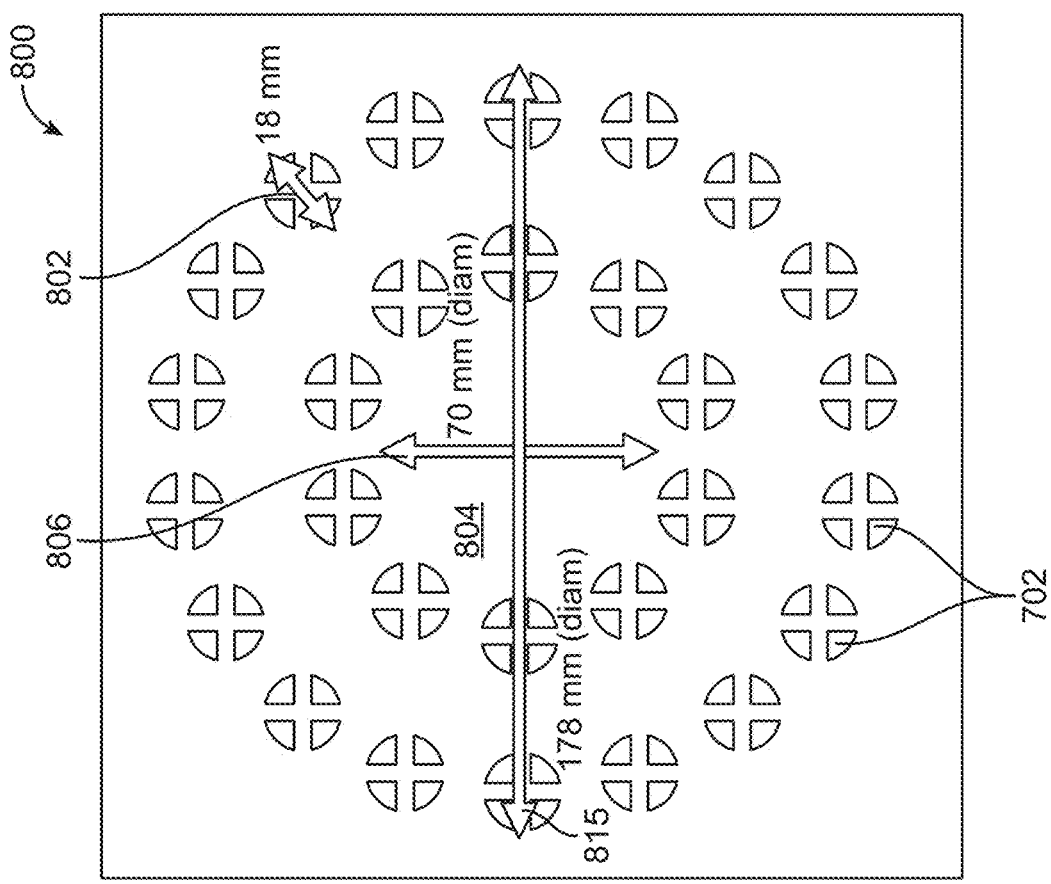
FIG. 8A shows stimuli on a screen to provide myopically defocused stimuli to the retina, in accordance with some embodiments.

FIG. 8A shows stimuli 702 on a screen 800 to provide myopically defocused stimuli to the retina, and FIG. 8B shows the corresponding dimensions of the myopically defocused stimuli on the retina in degrees. The size of the stimuli on the display is related to the distance between the user and the display, and the dimensions can be changed in accordance with the viewing distance to provide an appropriate angular subtense to the retina. One of ordinary skill in the art can readily perform calculations to determine the size of the stimuli on the display to provide appropriate angular sizing of the defocused projected images.

As shown in FIGS. 8A and 8B, each of the stimuli comprises a distance across 802, e.g. 18 mm, corresponding to an angular illumination 812 on the retina, e.g. 3.3 degrees. The stimuli are arranged on the display to provide a clear central field of view 804 having a distance across 806, for example 70 mm across, so as to provide an undisrupted central field of view 804 having a distance across 814 of 15 degrees. The plurality of stimuli comprises a maximum distance across 815, e.g. 178 mm, which corresponds to an angular subtense 816 of 35 degrees. The stimuli can be arranged with any appropriate object size in order to provide appropriate image size on the retina. Although reference is made to specific dimensions, any suitable dimensions can be used, for example by varying the distance to the eye and corresponding angular subtense. In some embodiments, the stimuli are arranged to provide a clear central field of view, for example 15 mm across, so as to provide an undisrupted central field of view of 15 degrees. In some embodiments, the plurality of stimuli comprises a maximum distance across, e.g. 70 mm, which corresponds to an angular subtense of 35 degrees.

Figure 9:
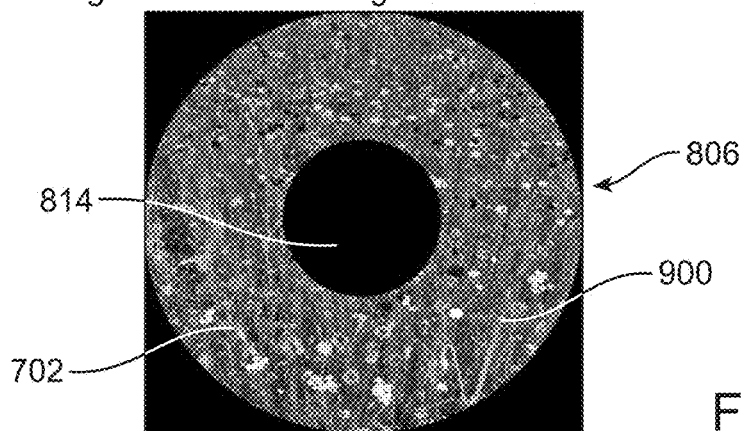
FIG. 9 shows a stimulus depicting a natural scene, such as an annular flower pattern, in accordance with some embodiments.

FIG. 9 shows a stimulus 702 depicting a natural scene 900, such as an annular flower pattern. Although a flower pattern is shown, any image can be used. The stimulus can be provided on a display alternatively or in combination with the stimulus 702 shown in FIGS. 8A and 8B, for example. The dimensions and angles of the stimulus shown in FIG. 9 can be dimensioned similarly to the stimulus shown in FIGS. 8A and 8B. For the central field of view 814 shown as a dark circle may comprise a distance across, for example corresponding to about 15 degrees, and the maximum distance 806 across the annular region can be about 35 degrees, for example. Work in relation to the present disclosure suggests that a polychromatic natural scene, such as a flower pattern may be more pleasant for the user. Work in relation to the present disclosure also suggests that in some embodiments, the polychromatic flower scene may be less effective as a stimulus than an annular array of white circles on a black background with a black cross segmenting the circular icon, although other stimuli may be used.

Figure 10:
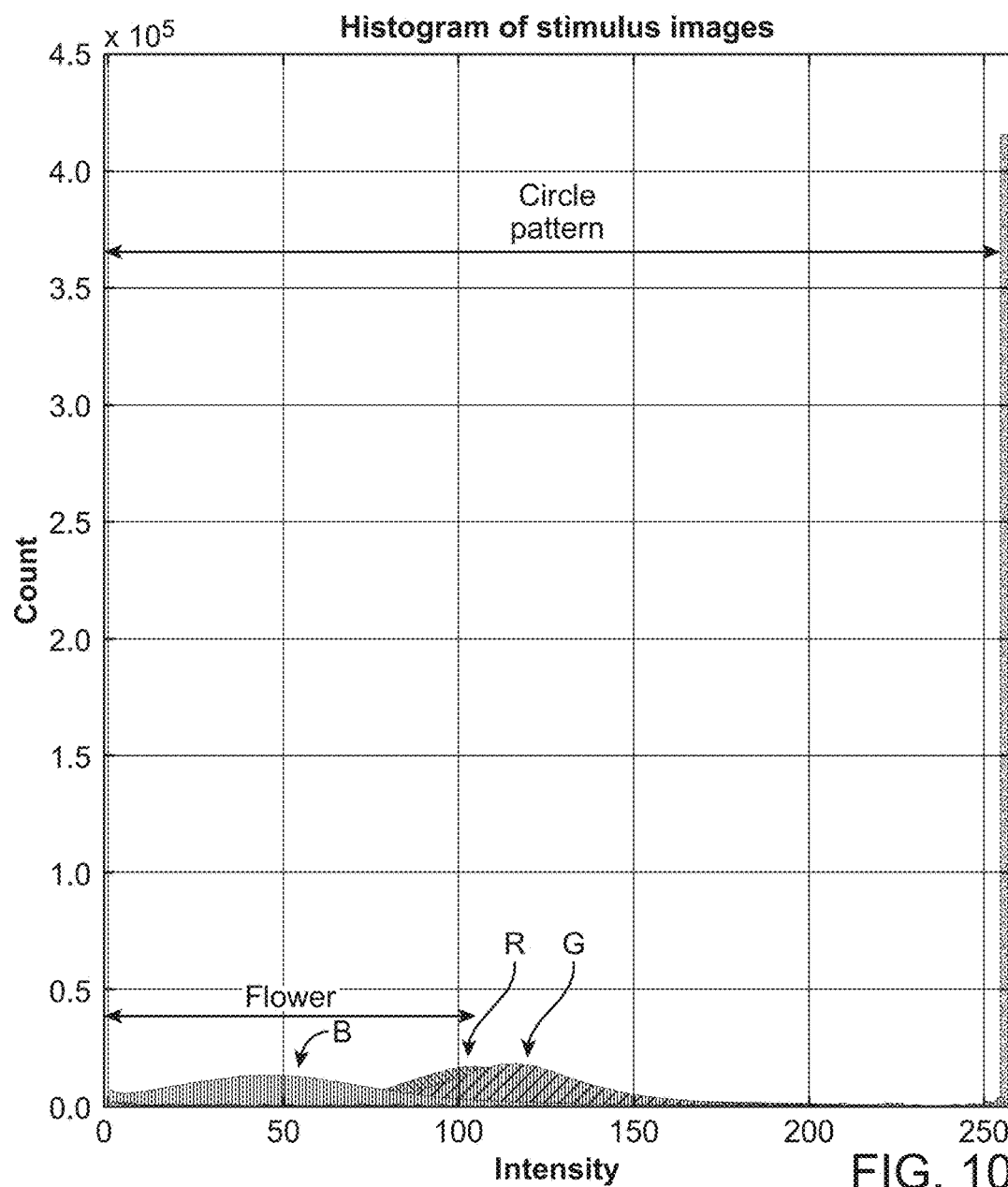
FIG. 10 shows image contrast and a histogram with red (R), blue (B) and green (G) values for the stimuli shown in FIGS. 8A to 9, in accordance with some embodiments.

FIG. 10 shows image contrast and a histogram with red (R), blue (B) and green (G) values for the stimuli shown in FIGS. 8A to 9. For the circle pattern as shown in FIGS. 9A and 9B, the histogram shows a pixel count of approximately $3.5 \times 10^5$ stimuli pixels with an intensity value of approximately 255. Black pixels have been excluded in histogram to increase clarity of graphical representation (Intensity=0). For the flower pattern shown in FIG. 9, the blue intensity distribution shows an intensity peak at about 50, a red peak at about 110 and a green peak at about 120, in which the counts are below $0.5 \times 10^5$.

In some embodiments, contrast is defined as separation between the lowest and the highest intensity of the image. The Global Contrast factor (GCF) can also be used to define the contrast of the stimulus images. The GCF measures the richness of details as perceived by a human observer. In some embodiments, the GCF of the stimulus is determined as described in *Global contrast factor-a new approach to image contrast* Matkovic, Kresimir et al., 2005; Computational Aesthetics in Graphics, Visualization and Imaging (2005); L. Neumann, M. Sbert, B. Gooch, W. Purgathofer (Editors).

The GCF values obtained are as follows:
Flower: 6.46
Circle pattern (b/w): 9.94

Work in relation to the present disclosure suggests that white Circles on black background may be preferred over flowers in a field because of higher GCF.

FIG. 11 shows an image 1100 suitable for modification and incorporation as a stimulus as described herein. The image 1100 may comprise a processed image to provide a suitable spatial frequency distribution as described herein. The image may comprise a natural image or a computer-generated image. The image can be masked so as to define an annular stimulus, e.g. similar to FIG. 9. FIG. 12 shows an image 1200 similar to the image of FIG. 11 that has been processed to provide an improved stimulus. This processed image can be masked digitally to form an annular stimulus as shown in FIG. 9, with appropriate spatial frequencies and contrast.

While the image can be processed in many ways, in some embodiments an image is processed with a digital spatial frequency filter and the contrast adjusted so as to provide an image with an appropriate spatial frequency distribution to generate an improved response of the eye. At a step in the process, the image is processed with a moving average filter having a length, for example a filter with a 400 pixel length. At another step, the RGB image is converted to a Grayscale image. At another step, the RGB image is adjusted according to the moving average image. At yet another step, the moving average filter is reapplied to the new image. In some embodiments, the moving average of the brightness is smoothed. For example, the initial image may have 100% difference in brightness, and the adjusted image has a 25% difference in brightness.

FIG. 13 shows an image of spatial frequencies distributions of the image of FIG. 11.

FIG. 14 shows an image of spatial frequencies distributions of the image of FIG. 12, which can be used as the stimulus in FIG. 9.

Figure 15:
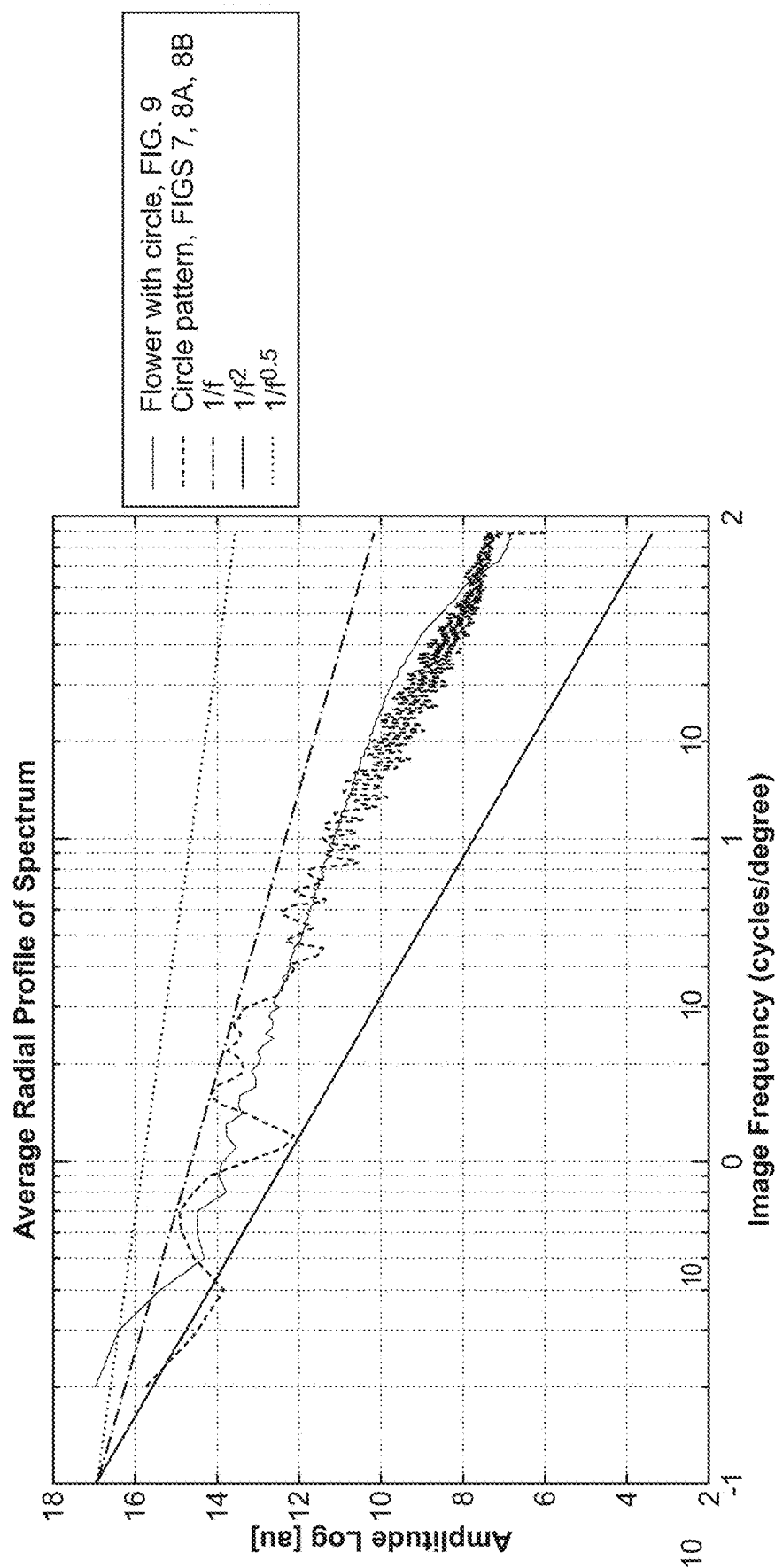
FIG. 15 shows a plot of image spatial frequency in cycles per degree and the log of the energy at each frequency for the stimulus images shown in FIGS. 8B and 9, in accordance with some embodiments.

FIG. 15 shows a plot of image spatial frequency in cycles per degree and the log of the energy at each frequency for the stimulus images shown in FIGS. 8B and 9. In the plot shown in FIG. 15, the average radial profile of the spatial frequency spectrum is shown, in which the amplitude log (arbitrary units, "au") is related to number density of features for a particular spatial frequency. For reference, this plot shows the $1/f$, $1/f^2$ and $1/f^{0.5}$ lines. The processed image comprising flower pattern with a circle shown in FIG. 9 has a similar frequency dependence to the white circle pattern with black crosses shown in FIGS. 7 to 8B. These plots show that the flower pattern and circle pattern both exhibit approximately $1/f$ slope dependencies at intermediate (e.g. mid-range) frequencies from about 2 to 10 cycles per degree. In some embodiments, the stimulus comprises a variation in intensity (energy, au) with a frequency dependence within a range from $1/f$ to $1/f^2$ frequency dependency for frequencies within a range from about 2 to 10 cycles per degree.

The stimulus can be configured in many ways with appropriate spatial frequency distributions, for example with a profile of spatial frequency distributions. In some embodiments, each of the plurality of stimuli comprises a length, edges, and an intensity profile distribution to generate spatial frequencies in a range of $1\times10^{-1}$ to $2.5\times10^1$ cycles per degree as imaged into the eye anterior or posterior to the retina and optionally within a range from $1\times10^{-1}$ to $1\times10^1$ cycles per degree. In some embodiments, the plurality of stimuli as imaged in the eye comprises a spatial frequency distribution providing a decrease in spatial frequency amplitude with an increase in spatial frequency for a range of spatial frequencies from about $1\times10^{-1}$ to about $5\times10^0$ cycles per degree. In some embodiments, the decrease in spatial frequency intensity is within a range from 1/(spatial frequency) to 1/(spatial frequency)$^2$ for the spatial frequency amplitude in arbitrary units. In some embodiments, the range of spatial frequencies is from about $3\times10^{-1}$ to about $1.0\times10^1$ cycles per degree and an optionally within a range from about $3\times10^{-1}$ to about $2.0\times10^0$ and further optionally within a range from about $3\times10^{-1}$ to about $1.0\times10^0$.

Alternatively or in combination with the spatial frequency properties, the stimulus can be configured with an appropriate ratio of stimulus intensity to background intensity. In some embodiments, a brightness of the plurality of defocused stimuli images is higher than a brightness of ambient illumination by a factor of at least 3 times the brightness of ambient illumination, optionally at least 5 times the brightness of background illumination, optionally within a range from 3 to 20 times the brightness of background illumination and further optionally within a range from 5 to 15 times the brightness of background illumination.

In some embodiments, the stimuli comprising the spatial frequency and intensity properties are presented with an appropriate ratio to one or more of background illumination or ambient illumination. In some embodiments, each of the plurality of stimuli as imaged in the eye is overlaid onto a substantially uniform grey background. In some embodiments, each of the plurality of stimuli comprises a polychromatic icon, e.g. a white icon, on a darker background to provide contrast, such that the icons have an edge profile or a total length of edges that generates features of spatial frequency predominantly in a range from $1\times10^{-1}$ cycles per degree to $2.5\times10^1$ cycles per degree, and optionally within a range from $1\times10^{-1}$ cycles per degree to $1\times10^1$ cycles per degree.

Figure 16:
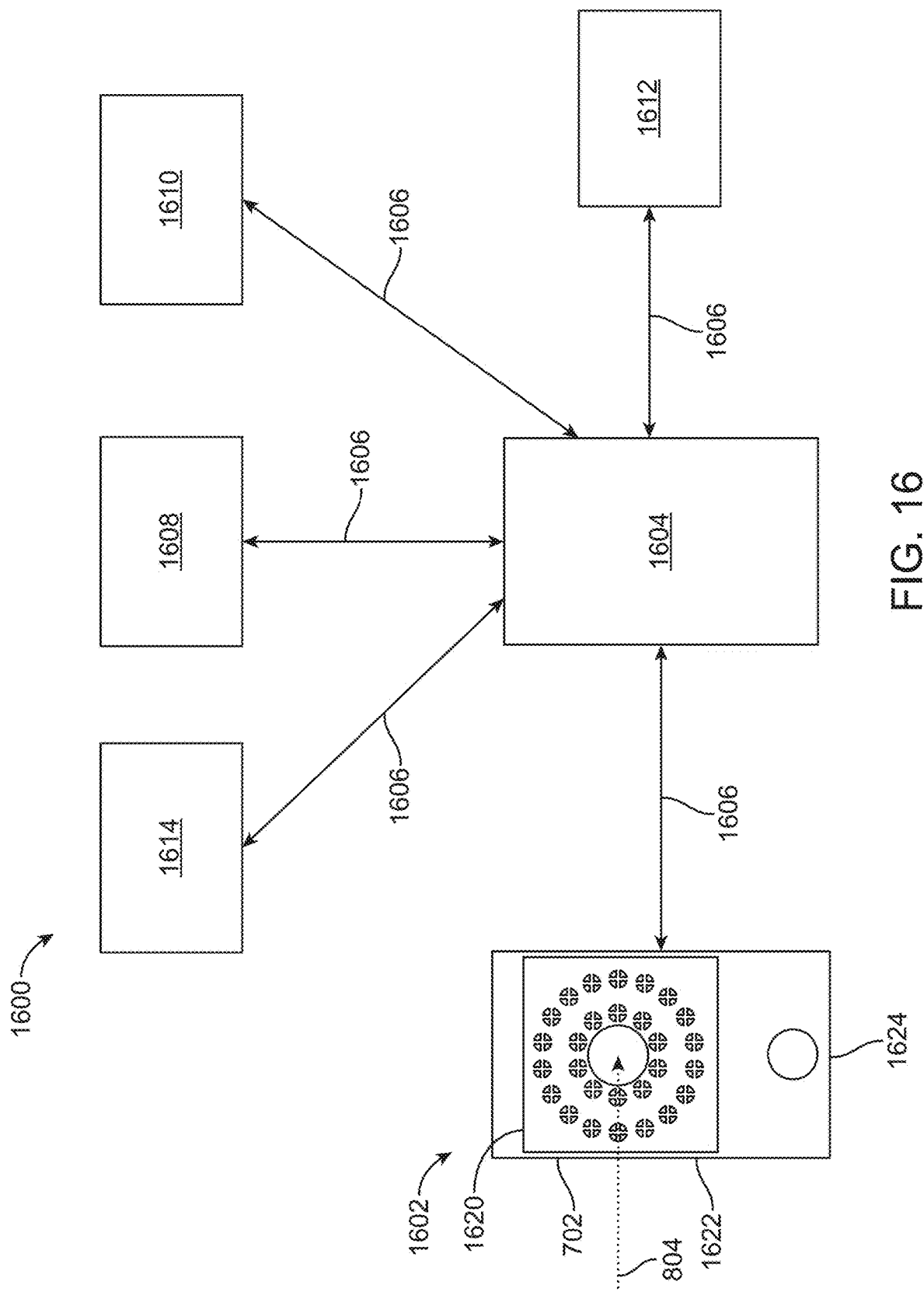
FIG. 16 shows a system for treating refractive error of the eye, in accordance with some embodiments.

FIG. 16 shows a system 1600 for treating refractive error of the eye. The system 1600 comprises a treatment device 1602, such as a user device operatively coupled to a server 1604 with a secure bi-directional communication protocol. The server 1604 is configured to communicate with a treatment professional device 1608 with a secure bidirectional communication protocol 1606. In some embodiments, the server 1608 is coupled to a caregiver device 1610 with a secure bidirectional communication protocol 1606. In some embodiments, the system 1600 comprises a treatment database 1612, which stores treatment parameters and results from a plurality of treatments. The treatment database 1602 can be configured to communicate with the server 1604 with secure bidirectional communication protocol 1606. In some embodiments, the treatment system 1600 comprises one or more clinical measurement devices 1614 configured to communicate with the server with a secure bidirectional communication protocol 1606. Each of the devices can be operatively coupled to another device with the secure bidirectional communication protocol 1606. The secure communication may comprise any suitable secure communication protocol that transmits encrypted data, and the data can be stored in any suitable encrypted format. The devices shown in FIG. 16 can be configured to comply with HIPAA and GDPR, for example, as will be appreciated by one of ordinary skill in the art. The server 1604 may comprise any suitable server such as a cloud-based server comprising a plurality of servers, which can be at different geographic locations. The treatment database 1612 may comprise a component of the server, although it is shown separately.

The treatment device 1602 can be configured in many ways as described herein, and may comprise a user device comprising one or more of an ophthalmic device, a TV screen, a computer screen, a virtual reality ("VR") display, an augmented reality ("AR") display, a handheld, a mobile computing device, a tablet computing device, a smart phone, a wearable device, a spectacle lens frame, a spectacle lens, a near eye display, a head-mounted display, a goggle, a contact lens, an implantable device, a corneal onlay, a corneal inlay, a corneal prosthesis, or an intraocular lens. For example, the treatment device 1602 may comprise an optical system with beam splitters as described herein. In some embodiments, the treatment device 1602 comprises a user device, such as a smart phone or tablet, for example. The display 1620 of the user device can be configured to provide a plurality of stimuli 702 as described herein. In some embodiments, the user device 1602 comprises a lenslet array 1622 placed over the plurality of stimuli 702, so as to provide an image 1624 of the stimuli 702 anterior or posterior to the retina. In some embodiments, each lenslet of the lenslet array is aligned with one of the plurality of stimuli. The user device can be configured with a clear viewing area 804 as described herein, for example without the lenslet array extending into the clear viewing area. The clear viewing area 804 can be configured for the user to view images, such as videos and allow the user to use the device in a substantially normal manner, for example so as to use a web browser, play video games, send and receive texts and emails, etc. The lenslet array 1622 can be positioned at a distance from the pixels so as to provide an appropriate amount of defocus as described herein. In some embodiments, the treatment system 1600 comprises one or more clinical measurement devices 1614.

The treatment professional device 1608 can be configured for the treatment professional to receive data from the user device 1602, such as treatment data. The treatment data may comprise any suitable treatment data, such as duration of treatment each day, daily use, screen time, screen time with the stimuli activated. The treatment professional device 1608, can also be configured to send and receive data from ophthalmic instruments, such as refraction data as described herein, in order to evaluate the efficacy of treatment. The treatment professional device 1608 can be configured to transmit treatment instructions to the user device 1602. The treatment instructions may comprise any suitable parameter as described herein, and may comprise a duration of and a time for treatment, for example. Work in relation to the present disclosure suggests that circadian rhythms may play a role in the efficacy of treatment, and the treatment instruction may comprise instructions for the user to perform the treatment at a time of day or a range of times, for example in the morning, for example at a time where the patient is located within a range from about 6 am to about 9 am local time.

The clinical measurement device 1614 may comprise any suitable clinical measurement device, such as one or more of an autorefractor or an OCT system, for example. Alternatively or in combination, the patient records such as manifest refraction can be stored at the clinical site and transmitted to the server.

The caregiver device 1610, may comprise any suitable device with a display, such as a smartphone or table. The caregiver device 1610 can be configured to transmit and receive data related to the treatment of the user. The caregiver device 1610 can be configured for a caregiver, such as a parent to monitor the treatment and promote compliance with a treatment protocol. For example, the server 1604 can be configured transmit notifications to the caregiver device 1610, such as notifications that the user is scheduled for treatment and the caregiver can interact with the user to encourage the user to receive treatment.

The treatment database 1612 can be configured to store data related to treatment. The data related to treatment may comprise treatment data and efficacy data, for example. The efficacy data may comprise one or more of refractive data and axial length data. The refractive data may comprise refractive data of the eyes of the user, e.g. sphere, cylinder and axis, at points in time, e.g. longitudinal data. The axial length data may comprise data such as OCT data collected at points in time. The treatment data 1612 may comprise data related to stimulus parameters as described herein, and may comprise duration of treatment at each day, intensity of stimulus, type of stimulus and defocus data, for example.

In some embodiments, algorithms such as artificial intelligence, machine learning, neural networks or convolutional neural networks are used to process the data to determined improved treatment parameters, such as duration of treatment, time of day of treatment, defocus, shape and intensity of the stimulus, amount of defocus, spatial frequencies of stimulus, ratio of stimulus to ambient light, background of stimulus, or any other parameter related to treatment. These parameters can be adjusted to provide improved treatment, and can be suggested to the treatment professional on the treatment professional device for the treatment professional to push the instructions to the user device.

While the treatment device 1602 such as the user device can be configured in many ways, in some embodiments the device 1602 comprises a sensor 1624 to detect one or more of luminosity or spectral data, such as a luminance sensor or a spectrophotometer. The sensor 1624 can be configured to measure and detect environmental light exposure of the subject such as a wearer or user. In some embodiments, the sensor is supported, e.g. mounted, on the treatment device as described herein, such as spectacles, a wearable device, or a user device.

The system of FIG. 16 is well suited for use with clinical trials to perform the clinical trial and generate efficacy data, for example.

Figure 17:
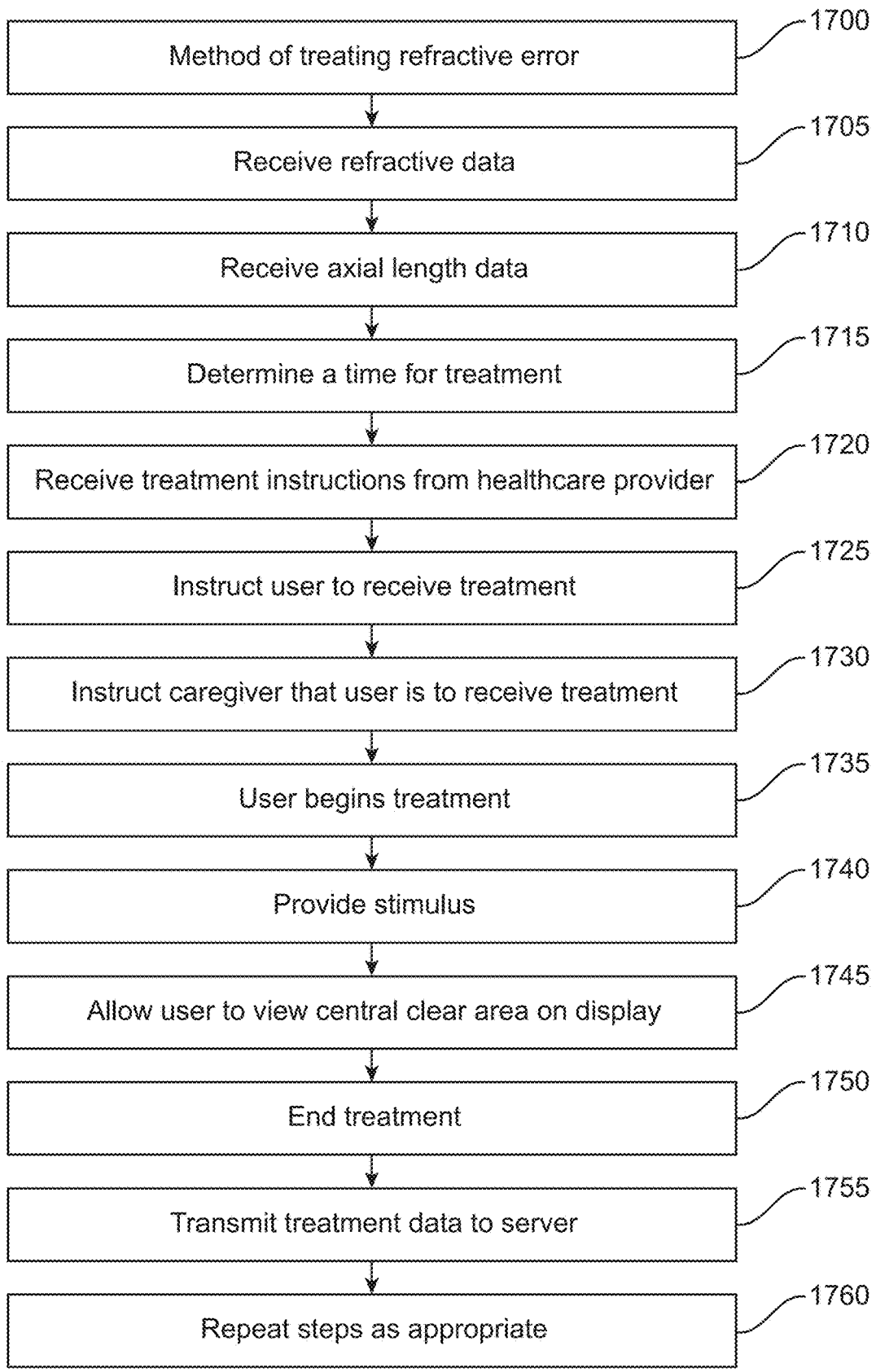
FIG. 17 shows a method of treating refractive error of the eye, in accordance with some embodiments.

FIG. 17 shows a method 1700 of treating refractive error of the eye.

At a step 1705 refractive data is received. The refractive data may comprise any suitable refractive data such as one or more of a manifest refraction, retinoscopy, a cycloplegic refraction, or an autorefraction. The refractive data may comprise one or more components of the refraction at a time of measurement, such as one or more of sphere, cylinder or axis.

At a step 1710, axial length data is received. The axial length data may comprise axial length data from the treated eye or a fellow eye, and the axial length data may comprise OCT data, for example.

At a step 1715, a time for treatment is determined the time for treatment may comprise one or more of a range of times for treatment, such as a time in the morning. The time for treatment may be based on a circadian rhythm of the patient, for example.

At a step 1720, treatment instructions are received from the healthcare provider. The treatment instructions may comprise any suitable parameter as described herein. For example, the treatment instructions may comprise one or more of a duration of treatment, an intensity of the stimuli, a shape of the stimuli, a background of the stimuli, a chrominance of the stimuli, a ratio of the intensity of the stimuli to the central viewing area, a ratio of the intensity of the stimuli to ambient illumination, a shape profile of the stimuli, a defocus of the stimuli, or a spatial frequency profile of the stimuli, for example.

At a step 1725, the user is instructed to receive treatment. The user can be instructed in many ways, for example with a prompt for the user to begin treatment, which the user can accept when the user is ready to begin treatment. The prompt may also comprise instructions for the user to begin treatment in an appropriate environment, for example an indoor environment. The prompt may provide an option for the user to delay treatment for an amount of time, for example for five minutes, and the user is prompted again at an appropriate time.

At a step 1730, the caregiver is instructed that user is to receive treatment, for example that it is time for the user to receive treatment. This can allow the caregiver, e.g. parent, to encourage the user to receive treatment.

At a step 1735, the user begins treatment. The user can initiate the treatment in many ways, for example with an input into the user device 1602. The input may comprise an input to a touchscreen display, for example. Alternatively or in combination, the user can respond to a prompt to receive treatment.

At a step 1740, the stimulus is provided to the user. The stimulus may comprise any suitable stimulus, for example a stimulus 702 as described herein.

At a step 1745, the user is allowed to view central clear area 804 on display. The user can view the data on the central clear area while the stimulus, e.g. stimuli, is provided.

At a step 1750, the treatment ends. The user can be informed that the treatment has ended. The caregiver can also be informed.

At a step 1755, treatment data is transmitted to a server 1604. The data can be transmitted to the healthcare provider 1608 or the treatment database 1612, for example.

At a step 1760, steps are repeated as appropriate. For example, a subsequent treatment can be provided to the user, and the user and caregiver notified of the subsequent treatment. Additional refractive data can be measured. Alternatively or in combination, additional OCT data can be measured.

Although FIG. 17 shows a method of treating refractive error in accordance with some embodiments, one of ordinary skill in the art will recognize many adaptations and variations. For example, the steps can be performed in any order, some of the steps omitted and some of the steps repeated. Also some of the steps may comprise sub-steps of other steps.

Any computing device, processor or combination thereof can be configured to perform one or more of the steps of FIG. 17.

Experimental Studies

Clinical studies on human subjects have been conducted to evaluate the efficacy on human subjects. The study involved a clinical test instrument, in which subjects were presented with a stimulus, and the efficacy of various stimuli and associated parameters evaluated.

Clinical Studies

The following study parameters were evaluated in a clinical study.

Figure 18A:
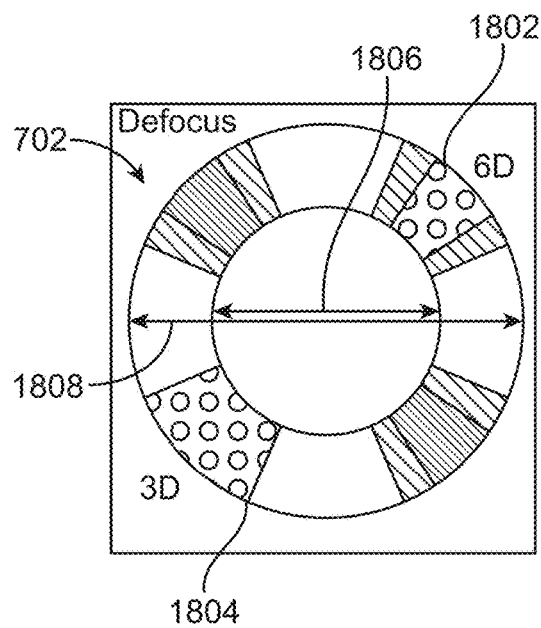
FIG. 18A depicts a stimulus with a myopic defocus of 6 D ("6 D stimulus") and another stimulus with a myopic defocus of 3 D ("3 D Stimulus"), in accordance with some embodiments.

1) Magnitude of myopic defocus. Values of 6 D, 4.5 D and 3 D of myopic defocus were evaluated. FIG. 18A depicts a stimulus 702 with a myopic defocus of 6 D ("6 D stimulus") region 1802 and another region 1804 with a myopic defocus of 3 D ("3 D Stimulus").

Figure 18B:
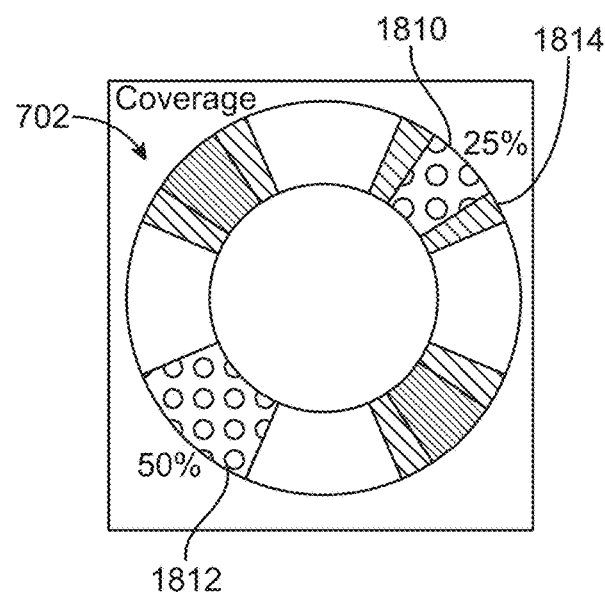
FIG. 18B depicts a stimulus with 25% coverage ("25% stimulus) and a stimulus with 50% coverage ("50% stimulus"), in accordance with some embodiments.

2) Coverage of the retina. The coverage corresponds to the percent of an annulus having an inner diameter 1806 corresponding to 15 degrees (full angle) and an outer diameter 1808 corresponding to about 35 degrees (full angle). The percent areas listed below correspond to the percent coverage of this annulus. The stimuli 702 tested included a segmented annulus 1814 with percentages of 70%, 50% and 25% of the full annulus. FIG. 18B depicts a stimulus 702 with a region 1810 with 25% coverage ("25% stimulus) and a region 1812 with 50% coverage ("50% stimulus").

Figure 18C:
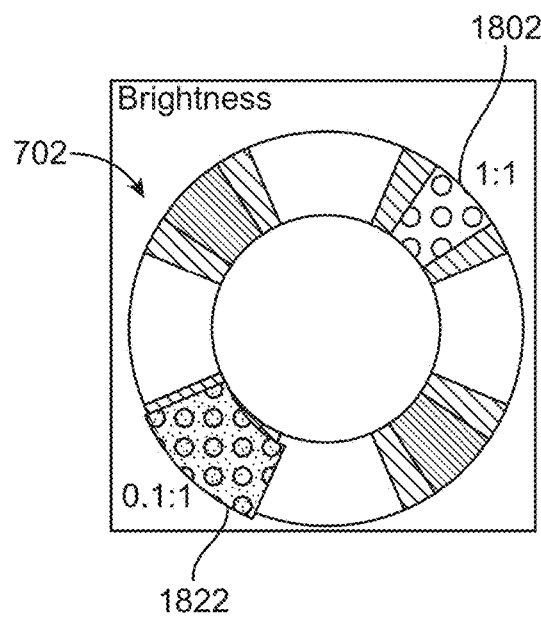
FIG. 18C depicts a stimulus with a brightness ratio of 0.1:1 and a stimulus with a 1:1 brightness ratio, in accordance with some embodiments.

3) Brightness over background image. The luminance of stimulus compared to the indoor lighting condition, $cd/m^2$ were evaluated with ratios of 1.0, 3.0, 5.0, 10.0 and 20.0. FIG. 18C depicts a stimulus 702 having a region 1820 with a brightness ratio of 0.1:1 and a region 1822 with a 1:1 brightness ratio.

Figure 18D:
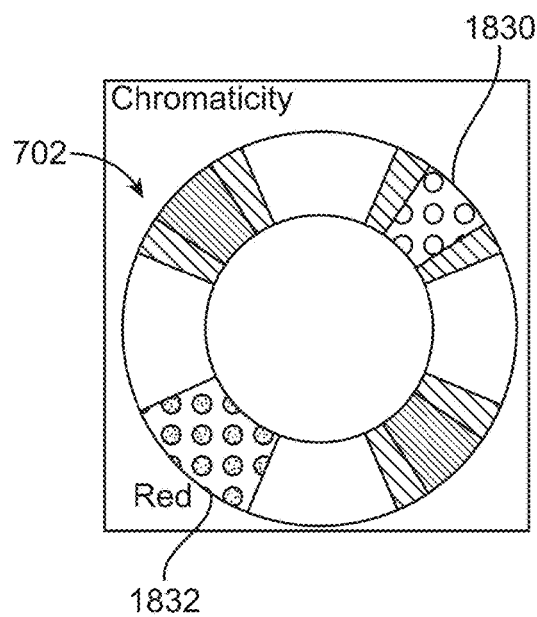
FIG. 18D depicts a black and white stimulus and a red stimulus, in accordance with some embodiments.

3) Chromaticity. Studies were conducted to determine the effect of monochromatic vs. white light, and the following chromaticity parameters were tested, white, green and red. FIG. 18D depicts stimulus 702 with a black and white stimulus region 1830 and a red stimulus region 1832.

4) Variation in spatial frequency content of stimulus. The spatial frequency content of the stimuli was assessed determine how the stimulus pattern influences the efficiency of the stimulus. Various patterns were tested, including a nature pattern as in FIG. 9, test circles comprising disks of brighter intensity as in FIGS. 18A to 18D and crossed dots as in FIGS. 8 to 9B.

Figure 19:
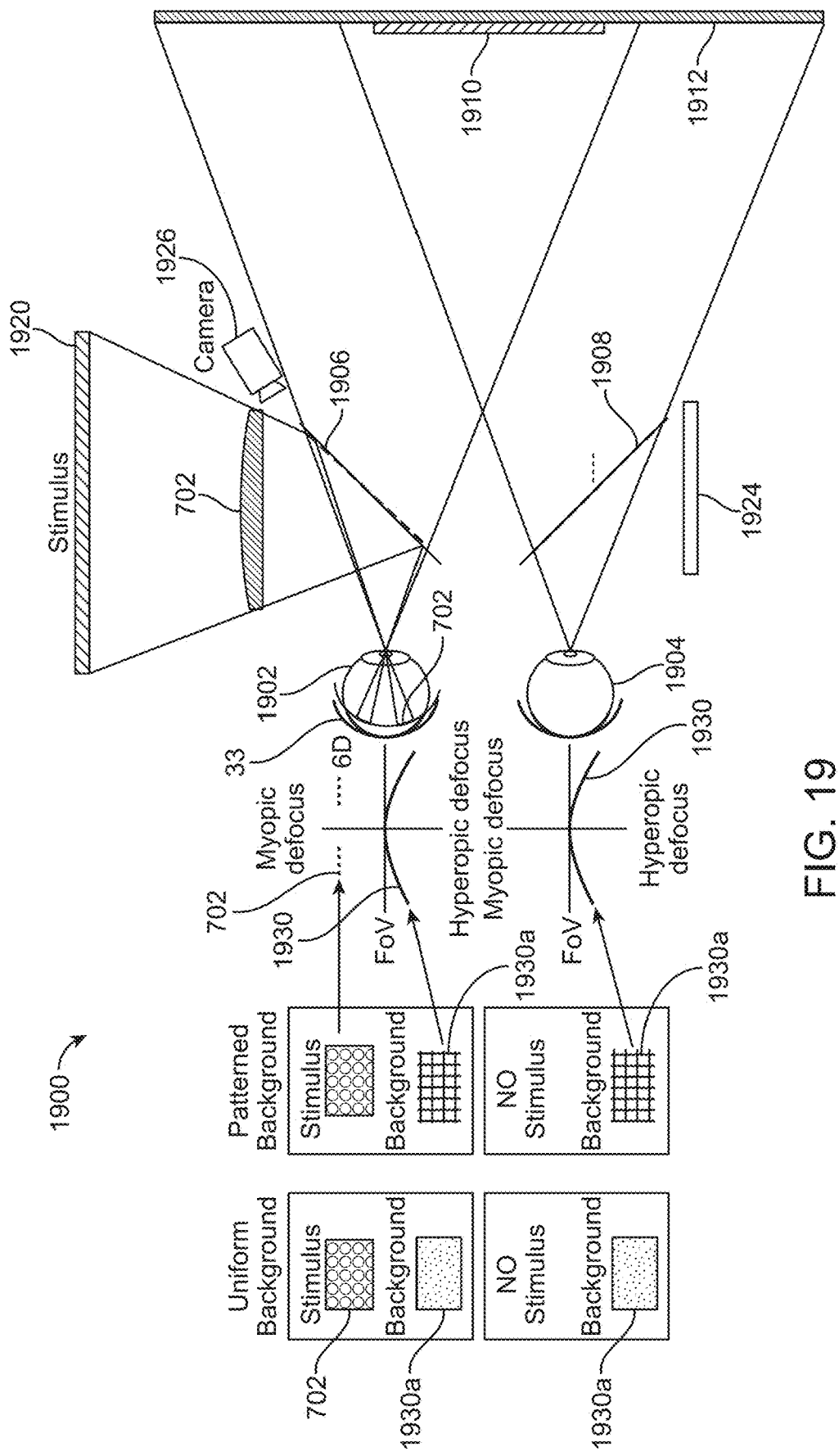
FIG. 19 depicts an optical system to project stimuli onto the retina, in accordance with some embodiments.

FIG. 19 depicts an optical system 1900 to project stimuli 702 onto the retina 33. In the studies conducted, the system 1900 comprised a bench top system. The system is configured to receive a left eye and a right eye of the subject for testing purposes. The test eye 1902 is placed in front of a first beam splitter 1906 and the control eye 1904 is placed in front of a second beam splitter 1908. The test eye 1902 and control eye 1904 are allowed to similarly view a central display 1910 in front of a passive background 1912. The display 1910 may comprise a clear central vision zone and show suitable content and may comprise a computer screen. In some embodiments, the central zone vision comprises an entertainment region as seen by the patient though the clear central vision zone with entertainment shown on the display. The active stimulation system comprises a table mounted device with head or chin rest. The system is configured to provide a background image at optical infinity for both eyes, and a video for central (foveal) vision. A stimulus 702 is shown on a display 1920 placed in front of a lens 1922 (e.g. an achromatic lens) to provide an overlaid stimulus image with a myopic defocus to the test eye. The myopic stimulus is projected anterior to the retina of the eye. The distance of the displayed stimulus from the lens 1922 and optical power of the lens 1922 are configured to provide an appropriate amount of defocus. The stimulus 702 is overlaid with the central display 1910 and passive background 1912 with the first beam splitter 1906. The second beam splitter 1908 is similar to the first beam splitter and background light blocked with an occlude 1924. The beam splitters comprised a reflectance and transmittance ratio of 50/50 for each eye, so as to transmit 50% of the light and to coupling 50% to the stimulus. The stimulus was provided on a screen, such as display 1920, at an appropriate distance from the achromatic lens.

The following parameters were adjusted as described herein, including, the magnitude of defocus, the coverage of the stimulus on the retina, e.g. the retinal image shell, dominance over the background image, e.g. contrast and brightness, and chromaticity, e.g. wavelength distribution.

Background patterns were also considered in these experiments. The background pattern may comprise a uniform pattern 1930a or a patterned background 1930b, e.g. a grid pattern. The background pattern was projected onto the peripheral retina with hyperopic defocus. In some embodiments, this hyperopic defocus is provided in order to push the point of focus of distant objects to optical infinity rather than the hyperfocal point. Work in relation to the present disclosure suggests that a patterned background may compete with the myopically defocused stimulus, and that a uniform background pattern may be preferred, in accordance with some embodiments. While the background can be presented in many ways, the background was presented as a poster with an appropriate test pattern.

A camera 1926 was used to observe one or more of the eyes. In the experiments conducted, the right eye was the test eye 1902, and the control eye 1904 was the left eye. Although FIG. 19 shows the left eye as the test eye and the right eye as the control eye, this can be readily changed by coupling the achromatic lens and display to the right eye and providing the occluder to the left eye. For example, the positions of the display with the stimulus pattern and the achromatic lens can be placed on the right side, and the occluder moved to the left side.

Figure 20A:
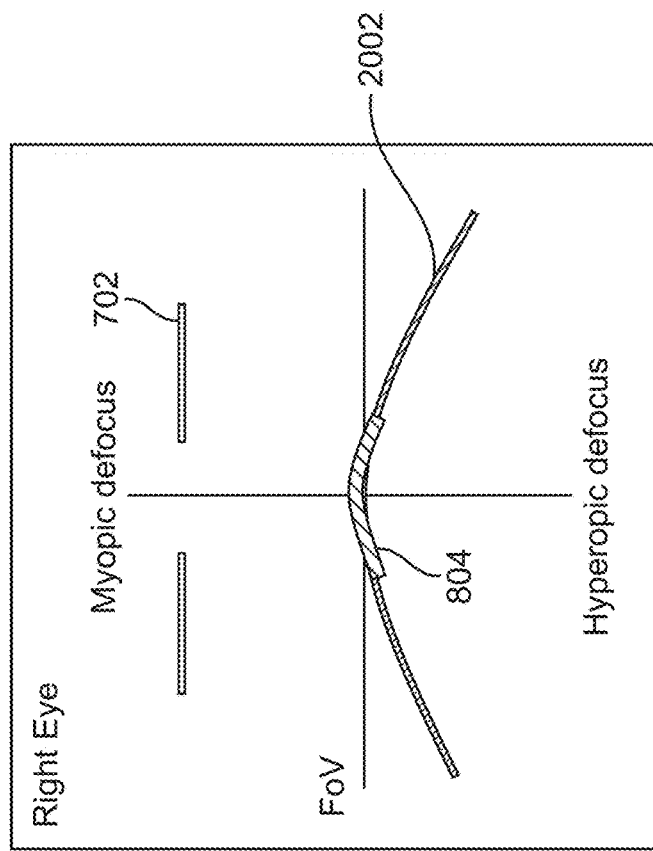
FIG. 20A shows the focus of the central entertainment region and the background pattern for the control eye, e.g. the left eye, in accordance with some embodiments.

FIG. 20A shows the focus of the clear central vision region 804, e.g. entertainment region, and the background pattern 1930 for the control eye, e.g. the left eye. The central region shown on the display to both eyes is presented to the user with no substantial refractive error, e.g. at optical infinity. The background pattern 1930 is also presented to the user at infinity. The retinal image shell 2002 is also shown. The background pattern was projected onto the peripheral retina with a hyperopic defocus, even though the central vision is corrected for an object (the computer display) at infinity.

Figure 20B:
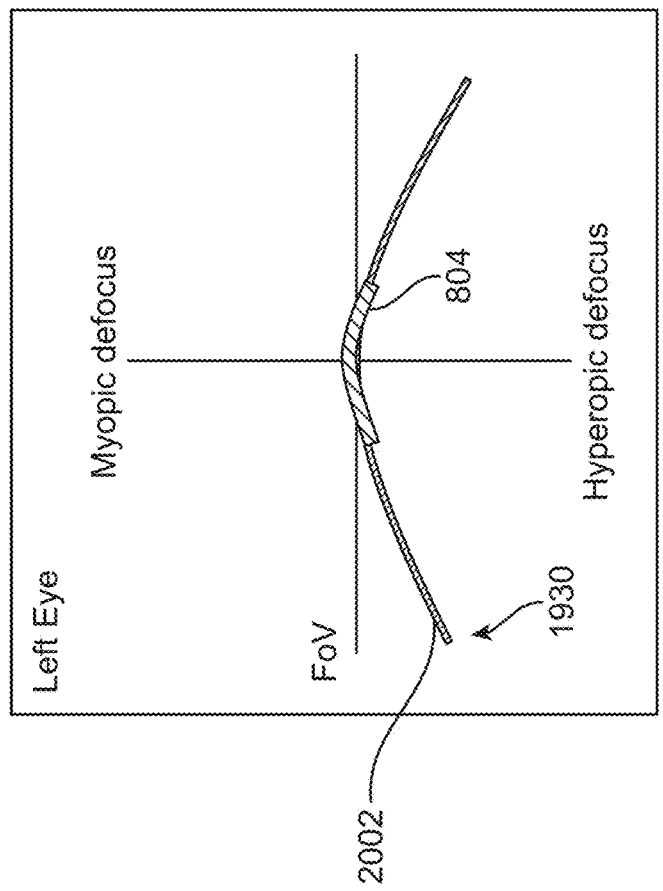
FIG. 20B shows the myopic defocus of the stimulus, the central entertainment region and the background pattern for the tested eye, e.g. the right eye, in accordance with some embodiments.

FIG. 20B shows the myopic defocus of the stimulus 702, the video being displayed in the central clear vision region 804 and the background pattern for the tested eye, e.g. the right eye. The optical configuration shows the stimulus as described herein imaged anterior to the retina with a myopic defocus.

These studies were conducted with a passive background comprising substantially uniform gray paper. The gray paper was illuminated with ceiling mounted adjustable lights. The brightness level was measured at 9-11 cd/m². The active display region comprising a central entertainment was provided with a television ("TV"). The brightness level of the TV was measured at 10 to 11 cd/m².

Although the ambient illumination of the room was measured at 500 lux to 700 lux, these values were controlled and reduced during the experimental tests.

The axial length and choroidal thickness of the eye were measured with an ambient illumination around 5-6 lux during measurement. The axial length and choroidal thickness were measured with a commercially available biometer and optical coherence tomography ("OCT") system, respectively.

During testing, the background illumination was 9-10 lux, and the TV screen was 9 to 10 lux.

Testing was carried out in the morning (usually 8:30 AM to 12:00 noon). The study was performed on the same subjects, after a wash out period of 1 hour. In other words, the subjects typically came into the office at 7:30-7:45 AM, spent 30-45 minutes relaxing (water, bathroom break, but no sweet snacks, coffee or caffeinated drinks), then he/she took the first test (1 hour stimulation), went through a 60 minute wash out session, in which they relaxed in a room by themselves, then went through the next stimulation step. All axial length measurements were referenced to the axial length measurements at the beginning of the day.

The peripheral stimulus was provided as a variable in these studies.

TABLE 1

Experimental results for a white stimulus on a black background.

| Brightness of Peripheral Stimulus | Decrease in axial length upon 1-hour stimulation (Test eye − control eye) |
|---|---|
| 9-10 lux (1×) | <1 micron (not significant) |
| 27-30 lux (3×) | 1 micron (not significant) |
| 45-50 lux (5×) | 1-2 micron (not significant) |
| 90-100 lux (10×) | 10 micron (significant at p = 0.05) |
| 180-200 lux (20×) | 10-12 micron (significant at p <= 0.05) |

These studies showed decreases in retinal thickness as measured by OCT. The brightness of the peripheral stimulus can be interpreted as a ratio brightness of the defocused stimulus to ambient illumination, e.g. the central display such as the TV screen or the background such as the gray paper. These studies show a decrease in axial length and increase in choroidal thickness for ratios of at least 3×, with statistically significant changes for ratios of at least 10×. These data suggest a ratio of the stimulus to ambient illumination within a range from 3× to at least 20×, for example within a range from 5× to 15×, such as 10×.

Figure 21:
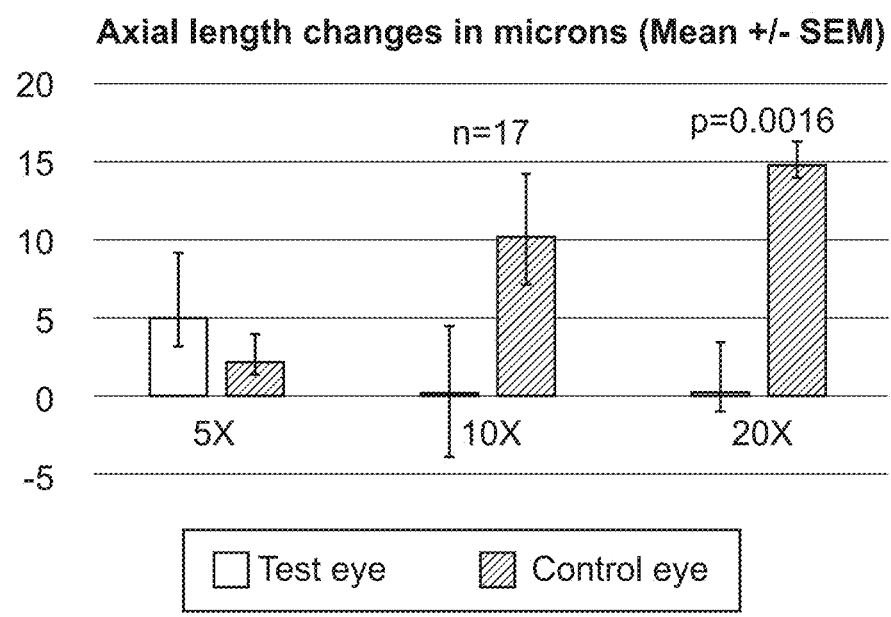
FIG. 21 shows clinical results similar to the results of Table 1, in accordance with some embodiments.

FIG. 21 shows clinical results similar to the results of Table 1. This data shows the effect of active stimulation of the peripheral retina with a myopically defocus projected image as described herein. The results were obtained with 1 hour of stimulation with a projected image comprising a white on black target as described herein. The subjects viewed a TV screen at 20 feet through a clear central zone as described herein. The axial length (corneal apex to retinal pigment epithelium "RPE") was measured without moving the subject. 192 data points were taken per measurement. Variation in axial length due to diurnal fluctuations was compensated for by measuring change in the test eye relative to the control eye in a paired manner. These results show nominal changes for the test eye (shown on left) versus the control eye (shown on right) for 5× stimulus illumination. However, for a ratio of stimulus to ambient of 10×, the test eye showed substantially greater decreases in axial length than the control eye. For the 20× stimulus illumination the difference was about 15 microns and statistically significant with a p value of 0.0016.

The above results were obtained with a white stimulus on a black background with a black cross extending through the white stimulus as shown with reference to FIGS. 8A and 8B. This stimulus comprises a spatial frequency distribution defined by a substantially linear relationship of amplitude to reciprocal spatial frequency in a range of spatial frequencies from about 0.1 to about 25 cycles per degree, for example from about 0.3 to about 10 cycles per degree, and optionally from about 0.1 to 5 cycles per degree.

Although the device used in these experiments comprises a monocular stimulation device, in some embodiments of the present disclosure the device comprises a binocular stimulation device.

Additional Clinical Study Results

The primary objective of this study was to measure the extent of axial length reduction and central choroidal thickening following defocus sessions under controlled conditions using the proposed system.

Twelve subjects with normal vision (nine males and three females) aged 21-32 years participated in the study (seven Asian, four Caucasian, and one Hispanic). The spherical equivalents of the test subjects were in the range 0.00 to −3.50 D, with an average of −0.70 D. The subjects underwent two defocus sessions, under photopic indoor light conditions, with an hour of discontinuation without defocus between the sessions. We used a non-wearable, augmented reality-based device to project digital defocus on the peripheral retina as described herein. The projected annular peripheral defocus stimulus extended from approximately a 15-degree diameter of the visual field outwards to a 35-degree diameter of the right eye as described herein.

Referring again to FIGS. 8A and 8B, these figures show the extent of the stimulus in millimeters (FIG. 8A) and degrees (FIG. 8B).

The system described herein has readily programmable control over important stimulus aspects for controlling eye growth including the size, retinal location, luminance, chromaticity, duration of activation, and dioptric magnitude of the peripheral defocus stimulus.

Referring again to FIG. 7, this image shows the subject's view through the test eye through the apparatus as described herein.

The left eye served as a control and did not receive any projected peripheral defocus. A gray backdrop served as the background for the projected defocus stimulus past the 15-degree diameter for both eyes. The content of the central aperture was a colored movie displayed on an HD television positioned 4 meters away, which served as a fixation zone. We set the test conditions of the digital projected stimulus to 5 times (5×), 10 times (10×), and 20 times (20×) the luminance of the gray poster background and the central 15-degree window (both of which were of equal luminance). The test conditions for the luminance ratio were randomized for each subject. Axial length measurements (Haag-Streit Lenstar APS900) and optical coherence tomography scans (Heidelberg Spectralis SD-OCT) of the posterior pole or macula were obtained before and after each defocus session.

The 5×, 10×, and 20× luminance ratios of the gray poster background test conditions underwent eight, nine, and seven trials, respectively, totaling twenty-four trials.

Figure 22:
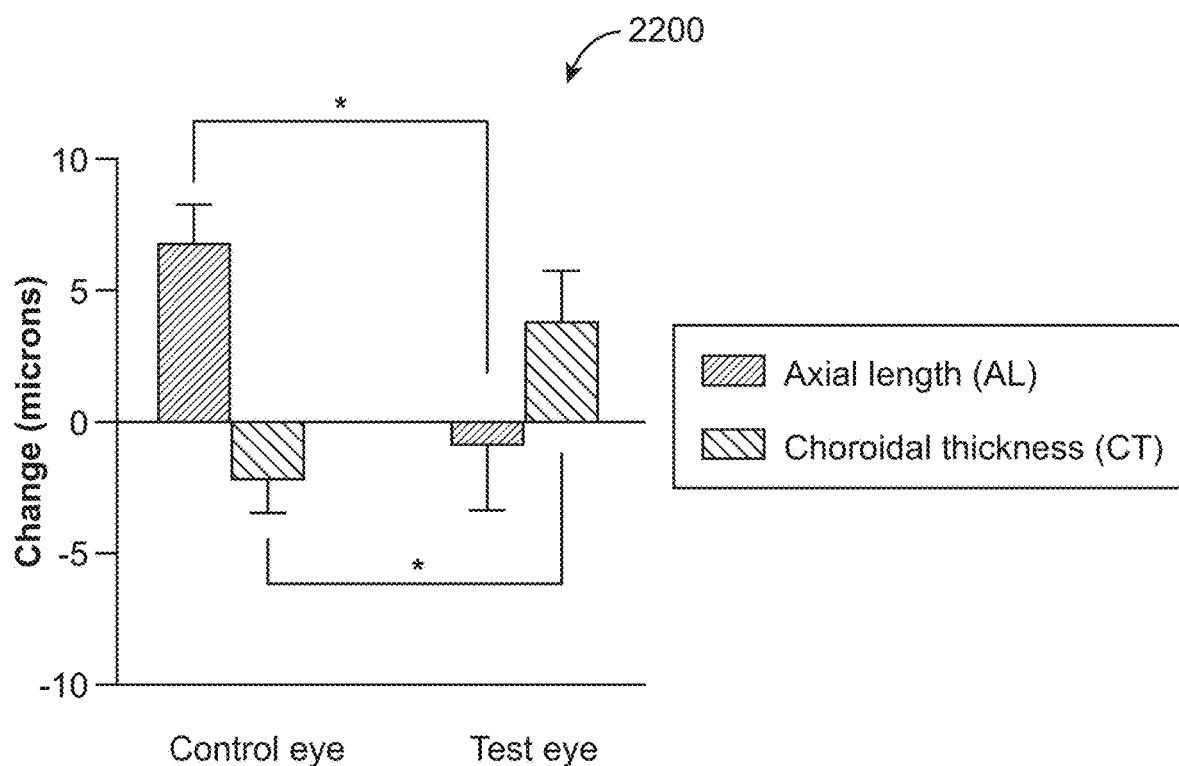
FIG. 22 shows the aggregate data of the 5×, 10×, and 20× luminance trials show that the mean change in central axial length (in microns) for the test eye was significantly smaller than that of the control eye (p<0.025) after the one-hour defocus sessions, in accordance with some embodiments.

FIG. 22 shows a chart 2200 of the aggregate data of the 5×, 10×, and 20× luminance trials show that the mean change in central axial length (in microns) for the test eye was significantly smaller than that of the control eye (p<0.025) after the one-hour defocus sessions. Similarly, the combined data from all trials reveal that the mean change in the subfoveal choroidal thickness was significantly greater in the test eyes than that in the control eyes (p<0.025) after the same defocus sessions. Both p-values correspond to the two-tailed t-test comparisons, with α=0.025 (Bonferroni correction).

Figure 23:
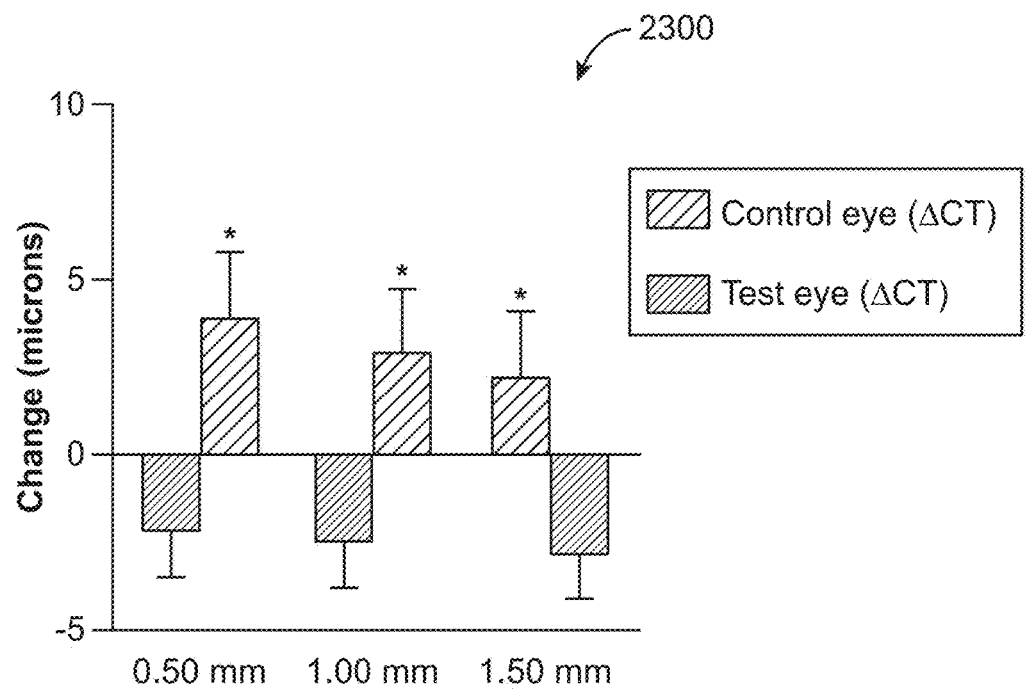
FIG. 23 shows the average change in axial length and choroidal thickness (mean±SEM): For the aggregate of all trials, the change in axial length for the test eye was significantly lower than that for the control eye after an hour of defocus sessions, in accordance with some embodiments.

FIG. 23 shows a chart 2300 of the average change in axial length and choroidal thickness (mean±SEM): For the aggregate of all trials, the change in axial length for the test eye was significantly lower than that for the control eye after an hour of defocus sessions. Similarly, the relative increase in the subfoveal choroidal thickness was also significantly higher in the test eye compared to the control eye after the defocus sessions (asterisk "*" refers to a p value less than or equal to 0.025, also referred to as "*=p<0.025").

The exact opposite behavior was observed in these two parameters for the control eye. The axial length in the test eye decreased by an average of approximately 1 micron, while it increased in the control eye by an average of about 7 microns. The subfoveal choroidal thickness increased in the test eye by an average of about 4 microns from the baseline, while it decreased on an average of about 2 microns in the control eye. The average relative effect for the test eye compared to the control eye was approximately an 8-micron decrease for the axial length, and an approximately 6-micron increase for the central choroidal thickness. The mean change in the central choroidal thickness measurements performed at 0.50 mm (subfoveal), 1.00 mm (parafoveal), and 1.50 mm (perifoveal) of the retinal eccentricity were each significantly different in the test eye versus the control eye (p<0.025), for all comparisons made before and after the defocus sessions. The central choroid thinned in each region in the control eye and thickened significantly after an hour of projected peripheral defocus sessions, as shown in FIG. 23.

FIG. 23 also shows relative thickening of the choroidal layer behind the retina (mean±SEM): The choroidal layer thickened significantly after an hour of projected defocus across 0.50 mm (subfoveal), 1.00 mm (parafoveal), and 1.50 mm (perifoveal) of retinal eccentricity in the posterior pole (*=p<0.025).

When considering the luminance ratio of each test, the 20× condition was the only one that showed statistical significance in the mean axial length change between the test and control eye (p=0.02) (independent t-test, two-tailed, uncorrected). Although the 20× luminance defocus stimulus condition performed more robustly than either the 5× or 10× stimuli, an increasing trend was seen in the difference between the test and control eyes as stimulus luminance increased compared to the background.

Our results show a statistically significant reduction of the axial length, and an increase in the choroidal thickness in the test eye, after 1-hour defocus sessions, as compared to the control eye. In addition, the central choroidal layer thickened significantly after an hour of projected defocus. One of the distinct advantages of this augmented reality-based system over conventional or multifocal defocus systems is that it allows for readily programmable control over important stimulus aspects. When testing several different luminosity intensities of the peripheral projected stimulus, we found an inverse correlation between increasing luminosity and decreasing axial length and a positive correlation between increasing luminosity and increasing choroidal thickness. The 20× test condition had a greater mean axial length change in the control eye after defocus, as compared to the mean change for the controls in the other two luminance test conditions. This is most likely due to the normal variability in the control eyes that occurs naturally without defocus. It may also have been due to a monocular coupling effect of the projected defocus, the binocular effects of which are yet to be understood. This exploratory study successfully proves the concept of utilizing an augmented reality-based peripheral defocus optical system for physiologically affecting ocular biometrics.

Our results and the versatile nature of the proposed method show promise for this concept of projected and programmable peripheral myopic defocus to help in efficiently understanding the role of the periphery in regulating eye growth and finding the fastest and most effective treatment strategies. Additionally, it can be applied to augmented reality and virtual reality devices, in-office treatments, spectacles, and contact lenses.

Referring again to FIGS. 1A to 3, 16, and 19, the stimulation apparatus can be configured to stimulate the eye with dilation of the pupil. Work in relation to the present disclosure suggests that increased diameter of the pupil, e.g. dilation of the pupil, can allow increased amounts of light to be provided to the peripheral portions of retina. The increased diameter of the pupil can be beneficial for increasing the eccentricity of illumination away from the fovea in order to illuminate regions of the retina farther from the fovea, and for increasing amounts of illumination to the peripheral regions of the retina. Work in relation to the present disclosure suggest that the surface area of the stimulated regions of the retina may be related to the efficacy of the response. Also, constriction of the pupil can be decreased by providing the stimulus to the peripheral regions of the retina while maintaining substantially lower illumination amounts of the fovea and macula during stimulation.

While the stimulation apparatus can be configured in many ways, in some embodiments, one or more optics are arranged to project the plurality of stimuli toward the peripheral portion of the retina when a pupil of the eye has been dilated. The pupil can be dilated in many ways, for example with decreased amounts of light so as to comprises a natural pupil, or with mydriatics such as cycloplegics so as to comprise a pharmacologically dilated pupil.

While the one or more stimuli, e.g. the plurality of stimuli, can be arranged to illuminate the retina with the pupil dilated in many ways, in some embodiments the one or more stimuli are arranged to illuminate the peripheral portion of the retina at an angle of at least 35 degrees from a visual axis of the eye.

In some embodiments, the stimulation apparatus comprises a sensor to measure a size of the pupil and a processor configured with instructions to direct the optical stimulus toward the eye in response to the size of the pupil. This can allow for increased amounts of light to the peripheral regions of the retina and in some instances a more accurate delivery and estimation of the amount of light delivered to the peripheral regions of the retina. While the size of the pupil can be measured in many ways, in some embodiments the size of the measured pupil comprises a diameter of the pupil. In some embodiments, the processor is configured to adjust one or more of an intensity or a duration of the optical stimulus in response to the size of the pupil. For example, a larger diameter pupil may receive the stimulus for a shorter time or lesser intensity, and a smaller diameter pupil may receive the stimulus for an increased amount of time or increased intensity. While the sensor to measure pupil size can be configured in any suitable way as will be known by one of ordinary skill in the art, in some embodiments the sensor comprises a sensor array. The sensor may comprise a sensor array of a camera, for example. The camera may comprise any suitable device such the patient mobile device, e.g. smart phone, or a measurement sensor built into a testing and measurement device as described herein.

In some embodiments, the plurality of stimuli is configured to allow dilation of a natural pupil when illuminated with plurality of stimuli. Work in relation to the present disclosure suggests that illumination of the peripheral portions of the retina has a less significant effect on pupil diameter than illumination of fovea or of the macula. In some embodiments, plurality of stimuli is configured to constrict the pupil by no more than one millimeter (mm) when the stimulus is provided as compared to a diameter of the pupil when the stimulus has not yet been provided.

In some embodiments, the pupil comprises a stimulation diameter when the eye is exposed to the plurality of stimuli, and the eye comprises a photopic diameter when the eye is exposed to photopic viewing conditions without the plurality of stimuli. In some embodiments, the photopic diameter is at least one millimeter smaller than the stimulation diameter. In some embodiments, the photopic viewing condition comprises a luminance of at least 3 Candela (cd) per meter squared (m$^2$).

In some embodiments, the stimulus is configured to illuminate the peripheral portion of the retina with an eccentricity of greater than 35 degrees with a pupil of the eye dilated by at least about 1 millimeter as compared to photopic illumination while the stimulus is provided to the peripheral retina with the eccentricity of greater than 35 degrees.

In some embodiments, no more than 10% of a total amount of energy of the plurality of stimuli is directed to a fovea of the eye in order to decrease constriction of the pupil in response to the plurality of stimuli and optionally no more than 5% of the total amount and optionally no more than 1% of the total amount.

In some embodiments, the stimulus comprises a photopic stimulus directed to the peripheral regions of the retina, and illumination of one or more of the fovea or macula comprises one or more of mesopic or scotopic illumination in order to decrease a size of the pupil. The apparatus can be configured in many ways to provide this stimulation. In some embodiments the apparatus comprises a display configured to provide the one or more of the mesopic or scotopic illumination and the plurality of stimuli are configured in any suitable way to provide the photopic illumination as described herein.

In some embodiments, a method of treating a refractive error of an eye, the method comprises dilating a pupil of the eye, and providing an optical stimulus to a peripheral portion of the retina decrease the refractive error of the eye. The stimulus may comprise any suitable stimulus as described herein, and may comprise a plurality of stimuli.

While the pupil can be dilated in many ways, in some embodiments, the pupil is dilated with a mydriatic. While any suitable mydriatic can be used to pharmacologically increase the size of the pupil, in some embodiments, the mydriatic comprises a cycloplegic.

In some embodiments, the cycloplegic is selected from the group consisting of atropine, cyclopentolate, homatropine, scopolamine and tropicamide. For example, the cycloplegic may comprises atropine with an appropriate percentage. In some embodiments, the percentage by weight within a range from 0.025% to 0.2% and optionally from 0.05% to 0.1%.

In some embodiments, a size of the pupil is measured and the optical stimulus is directed toward the eye in response to the size of the pupil, and one or more of an intensity or a duration of the optical stimulus is adjusted in response to the size of the pupil. In some embodiments, the size of the pupil is measured with a sensor such a sensor array, and the sensor array comprises a sensor array of a camera, for example.

In some embodiments, the pupil comprises natural pupil of the eye dilated with an appropriate amount of illumination of the peripheral retina and light from other sources passing through the natural pupil, such that the natural pupil is capable of constricting and dilating in response to illumination to the eye.

In some embodiments, the natural pupil is dilated with a mesopic background illumination or a scotopic background illumination.

In some embodiments, the natural pupil constricts by no more than one millimeter (mm) when the stimulus is provided as compared to a diameter of the natural pupil when the stimulus has not yet been provided.

In some embodiments, the natural pupil comprises a stimulation diameter when the eye is exposed to the stimulus, and wherein the natural pupil comprises a photopic diameter when the eye is exposed to photopic viewing conditions. In some embodiments, and the photopic diameter is at least one millimeter smaller than the stimulation diameter.

In some embodiments, the stimulus is configured to illuminate the peripheral retina with an eccentricity of greater than 35 degrees with the pupil dilated by at least about 1 millimeter as compared to photopic illumination while the stimulus is provided to the peripheral retina with the eccentricity of greater than 35 degrees.

While the stimulus can be configured in many ways to decrease pupil constriction, in some embodiments, no more than 10% of a total amount of energy of the plurality of stimuli is directed to a fovea of the eye in order to decrease constriction of the pupil in response to the plurality of stimuli and optionally no more than 5% of the total amount and optionally no more than 1% of the total amount.

In some embodiments, the stimulus comprises a photopic stimulus directed to the peripheral regions of the retina and wherein illumination of one or more of the fovea or macula comprises one or more of mesopic or scotopic illumination in order to decrease a size of the pupil.

As described herein, the computing devices and systems described and/or illustrated herein broadly represent any type or form of computing device or system capable of executing computer-readable instructions, such as those contained within the modules described herein. In their most basic configuration, these computing device(s) may each comprise at least one memory device and at least one physical processor.

The term "memory" or "memory device," as used herein, generally represents any type or form of volatile or non-volatile storage device or medium capable of storing data and/or computer-readable instructions. In one example, a memory device may store, load, and/or maintain one or more of the modules described herein. Examples of memory devices comprise, without limitation, Random Access Memory (RAM), Read Only Memory (ROM), flash memory, Hard Disk Drives (HDDs), Solid-State Drives (SSDs), optical disk drives, caches, variations or combinations of one or more of the same, or any other suitable storage memory.

In addition, the term "processor" or "physical processor," as used herein, generally refers to any type or form of hardware-implemented processing unit capable of interpreting and/or executing computer-readable instructions. In one example, a physical processor may access and/or modify one or more modules stored in the above-described memory device. Examples of physical processors comprise, without limitation, microprocessors, microcontrollers, Central Processing Units (CPUs), Field-Programmable Gate Arrays (FPGAs) that implement softcore processors, Application-Specific Integrated Circuits (ASICs), portions of one or more of the same, variations or combinations of one or more of the same, or any other suitable physical processor. The processor may comprise a distributed processor system, e.g. running parallel processors, or a remote processor such as a server, and combinations thereof.

Although illustrated as separate elements, the method steps described and/or illustrated herein may represent portions of a single application. In addition, in some embodiments one or more of these steps may represent or correspond to one or more software applications or programs that, when executed by a computing device, may cause the computing device to perform one or more tasks, such as the method step.

In addition, one or more of the devices described herein may transform data, physical devices, and/or representations of physical devices from one form to another. Additionally or alternatively, one or more of the modules recited herein may transform a processor, volatile memory, non-volatile memory, and/or any other portion of a physical computing device from one form of computing device to another form of computing device by executing on the computing device, storing data on the computing device, and/or otherwise interacting with the computing device.

The term "computer-readable medium," as used herein, generally refers to any form of device, carrier, or medium capable of storing or carrying computer-readable instructions. Examples of computer-readable media comprise, without limitation, transmission-type media, such as carrier waves, and non-transitory-type media, such as magnetic-storage media (e.g., hard disk drives, tape drives, and floppy disks), optical-storage media (e.g., Compact Disks (CDs), Digital Video Disks (DVDs), and BLU-RAY disks), electronic-storage media (e.g., solid-state drives and flash media), and other distribution systems.

A person of ordinary skill in the art will recognize that any process or method disclosed herein can be modified in many ways. The process parameters and sequence of the steps described and/or illustrated herein are given by way of example only and can be varied as desired. For example, while the steps illustrated and/or described herein may be shown or discussed in a particular order, these steps do not necessarily need to be performed in the order illustrated or discussed.

The various exemplary methods described and/or illustrated herein may also omit one or more of the steps described or illustrated herein or comprise additional steps in addition to those disclosed. Further, a step of any method as disclosed herein can be combined with any one or more steps of any other method as disclosed herein.

The processor as described herein can be configured to perform one or more steps of any method disclosed herein. Alternatively or in combination, the processor can be configured to combine one or more steps of one or more methods as disclosed herein.

Unless otherwise noted, the terms "connected to" and "coupled to" (and their derivatives), as used in the specification and claims, are to be construed as permitting both direct and indirect (i.e., via other elements or components) connection. In addition, the terms "a" or "an," as used in the specification and claims, are to be construed as meaning "at least one of." Finally, for ease of use, the terms "including" and "having" (and their derivatives), as used in the specification and claims, are interchangeable with and shall have the same meaning as the word "comprising.

The processor as disclosed herein can be configured with instructions to perform any one or more steps of any method as disclosed herein.

It will be understood that although the terms "first," "second," "third", etc. may be used herein to describe various layers, elements, components, regions or sections without referring to any particular order or sequence of events. These terms are merely used to distinguish one layer, element, component, region or section from another layer, element, component, region or section. A first layer, element, component, region or section as described herein could be referred to as a second layer, element, component, region or section without departing from the teachings of the present disclosure.

As used herein, the term "or" is used inclusively to refer items in the alternative and in combination.

As used herein, characters such as numerals refer to like elements.

The present disclosure includes the following numbered clauses:

Clause 1. An apparatus for treating refractive error of an eye, the apparatus comprising: a plurality of stimuli; and one or more optics to image the plurality of stimuli anterior or posterior to a peripheral portion of the retina to form a plurality of defocused images on a peripheral portion of the retina; wherein the plurality of stimuli and the one or more optics are arranged to reduce interference with a central vision of the eye.

Clause 2. The apparatus of clause 1 wherein said plurality of images is defocused by an amount within a range from 3.0 D to 6.0 D, optionally myopically defocused, and optionally within a range from 3.5 D to 5.0 D.

Clause 3. The apparatus of clause 1 wherein a brightness of said plurality of defocused images is higher than a brightness of background illumination by a factor of at least 3, optionally at least 5 times the brightness of background illumination, optionally within a range from 3 to 20 times the brightness of background illumination and further optionally within a range from 5 to 15 times the brightness of background illumination.

Clause 4. The apparatus of clause 1 wherein each of said plurality of defocused images comprises an intensity profile distribution, the intensity profile distribution comprising one or more peaks distributed around an inner portion with a decreased intensity relative to the one or more peaks.

Clause 5. The apparatus of clause 4, wherein the one or more peaks comprises a plurality of peaks and wherein the inner portion is located between the plurality of peaks.

Clause 6. The apparatus of clause 5, wherein the plurality of peaks comprises four peaks and the inner portion is located between the four peaks.

Clause 7. The apparatus of clause 6, wherein the inner portion comprises a cross extending between the four peaks.

Clause 8. The apparatus of clause 4, wherein the one or more peaks comprises an annular peak and wherein the inner portion is located within the annular peak.

Clause 9. The apparatus of clause 1 wherein each of said plurality of defocused images comprises a polychromatic icon on a darker background to provide contrast and optionally wherein the polychromatic icon comprises a white icon and said darker background comprises a substantially black background.

Clause 10. The apparatus of clause 1, wherein each of the plurality of stimuli comprises a length, edges, and an intensity profile distribution to generate spatial frequencies in a range of $1\times10$-1 to $2.5\times101$ cycles per degree as imaged into the eye anterior or posterior to the retina and optionally within a range from $1\times10$-1 to $1\times101$ cycles per degree.

Clause 11. The apparatus of clause 1 wherein said plurality of stimuli as imaged in the eye comprises a spatial frequency distribution providing a decrease in spatial frequency amplitude with an increase in spatial frequency for a range of spatial frequencies from about $1\times10$-1 to about $2.5\times101$ cycles per degree and optionally from $1\times10$-1 to about $5\times100$ cycles per degree.

Clause 12. The apparatus of clause 11, wherein the decrease in spatial frequency intensity is within a range from 1/(spatial frequency)0.5 to 1/(spatial frequency)2 for the spatial frequency amplitude in arbitrary units and optionally from 1/(spatial frequency) to 1/(spatial frequency)2 for the spatial frequency amplitude in arbitrary units.

Clause 13. The apparatus of clause 11, wherein the range of spatial frequencies is from about $3\times10$-1 to about $1.0\times101$ cycles per degree and optionally within a range from about $3\times10$-1 to about $2.0\times100$ and further optionally from about $3\times10$-1 to about $1.0\times100$.

Clause 14. The apparatus of clause 1, wherein the apparatus is configured for mono-ocular stimulation of the eye of the patient.

Clause 15. The apparatus of clause 1, wherein the apparatus is configured for binocular stimulation of the patient.

Clause 16. The apparatus of clause 15, further comprising: a second plurality of stimuli to stimulate the fellow eye of the patient; and a second one or more optics to image the second plurality of stimuli anterior or posterior to a peripheral portion of a retina of the fellow eye to form a second plurality of defocused images on the peripheral portion of the second retina; wherein the second plurality of stimuli and the second one or more optics are arranged to reduce interference with a central vision of the fellow eye.

Clause 17. The apparatus of clause 1 the plurality of stimuli and the one or more optics are arranged to provide a substantially uninterrupted field of view within a range from 10 degrees to 30 degrees, optionally from 10 degrees to 20 degrees and optionally within a range from 12 degrees to 18 degrees, and optionally wherein each of said plurality of defocused images is projected onto the retina outside the field of view.

Clause 18. The apparatus of clause 1, wherein each of the plurality of stimuli as imaged in the eye is overlaid onto a substantially uniform grey background, said each of the plurality of stimuli comprising a white icon, such that said icons have a total length of edges that generate features of spatial frequency predominantly in a range from $1\times10$-1 cycles per degree to $2.5\times101$ cycles per degree and optionally within a range from $1\times10$-1 cycles per degree to $1\times101$ cycles per degree.

Clause 19. The apparatus of clause 1, wherein each of the plurality of stimuli as imaged in the eye comprises a polychromatic icon having an edge profile on a background that generates features of spatial frequency predominantly in a range from $1\times10$-1 cycles per degree to $2.5\times101$ cycles per degree and optionally within a range from $1\times10$-1 cycles per degree to $1\times101$ cycles per degree.

Clause 20. The apparatus of clause 1 wherein each of the plurality of stimuli comprises a global contrast factor greater than 0.7 and optionally greater than 8.0.

Clause 21. The apparatus of clause 1, wherein the one or more optics comprises one or more of a hologram, a waveguide, a mirror, a lens, a spectacle lens, or a contact lens.

Clause 22. The apparatus of clause 1, further comprising a support to couple to the user to support the one or more optics, the support comprising a component of one or more of a head mounted device, a spectacle lens, an eyeglass frames, goggles, an AR display, a contact lens, or a VR display.

Clause 23. The apparatus of clause 1, further comprising a lens to correct a refractive error of the eye.

Clause 24. The apparatus of clause 1, wherein the one or more optics are arranged to project the plurality of stimuli toward the peripheral portion of the retina when a pupil of the eye has been dilated with a mydriatic.

Clause 25. The apparatus of clause 24 wherein the plurality of stimuli is arranged to illuminate the peripheral portion of the retina at an angle of at least 35 degrees from a visual axis of the eye.

Clause 26. The apparatus of clause 1, further comprises a sensor to measure a size of the pupil and further comprising a processor configured with instructions to direct the optical stimulus toward the eye in response to the size of the pupil and optionally wherein the size of the pupil comprises a diameter of the pupil.

Clause 27. The apparatus of clause 26, wherein the processor is configured to adjust one or more of an intensity or a duration of the optical stimulus in response to the size of the pupil.

Clause 28. The apparatus of clause 26, wherein the sensor comprises a sensor array and optionally wherein the sensor array comprises a sensor array of a camera.

Clause 29. The apparatus of clause 26, wherein the plurality of stimuli is configured to allow dilation of a natural pupil when illuminated with plurality of stimuli.

Clause 30. The apparatus of clause 1, wherein plurality of stimuli is configured to constrict the pupil by no more than one millimeter (mm) when the stimulus is provided as compared to a diameter of the pupil when the stimulus has not yet been provided.

Clause 31. The apparatus of clause 1, wherein the pupil comprises a stimulation diameter when the eye is exposed to the plurality of stimuli and wherein the eye comprises a photopic diameter when the eye is exposed to photopic viewing conditions without the plurality of stimuli, and wherein the photopic diameter is at least one millimeter smaller than the stimulation diameter and optionally wherein the photopic viewing condition comprises a luminance of at least 3 Candela (cd) per meter squared (m2).

Clause 32. The apparatus of clause 1, wherein the stimulus is configured to illuminate the peripheral portion of the retina with an eccentricity of greater than 35 degrees with a pupil of the eye dilated by at least about 1 millimeter as compared to photopic illumination while the stimulus is provided to the peripheral retina with the eccentricity of greater than 35 degrees.

Clause 33. The apparatus of clause 1, wherein no more than 10% of a total amount of energy of the plurality of stimuli is directed to a fovea of the eye in order to decrease constriction of the pupil in response to the plurality of stimuli and optionally no more than 5% of the total amount and optionally no more than 1% of the total amount.

Clause 34. A method of treating a refractive error of an eye, the method comprising: providing a stimulus to a peripheral region of a retina of the eye, wherein the stimulus is provided in a morning.

Clause 35. The method of clause 34, wherein the stimulus is provided by an apparatus as in any one of the preceding clauses.

Clause 36. The method of clause 34, wherein the stimulus is provided between 6 am and 10 am.

Clause 37. The method of clause 34, wherein the stimulus is provided between 6 am and 10 am.

Clause 38. The method of clause 34, wherein the stimulus is provided to the eye on a plurality of adjacent days, in the morning, and wherein a total treatment time on each day comprises no more than an hour.

Clause 39. A tangible medium configured with instructions to be executed by a processor, the tangible medium configured to perform the method of any one of clauses 34 to 38.

Clause 40. A patient database comprising: treatment data corresponding to a plurality of retinal stimulation treatments for a plurality of patients; and efficacy data for the plurality of patients, the efficacy data comprising refractive data for the plurality of treatments.

Clause 41. A method of conducting a clinical trial, the method comprising: providing peripheral retinal stimulation to a test eye and not to a control eye on each day of a plurality of days; measuring axial lengths of the test eye and the control eye before and after treatment on each day of a plurality of days; and comparing axial lengths of the test eye to axial lengths of the control eye to determine efficacy of the peripheral retinal stimulation.

Clause 42. A method of treating a refractive error of an eye, the method comprising: dilating a pupil of the eye; and providing an optical stimulus to a peripheral portion of the retina decrease the refractive error of the eye.

Clause 43. The method of clause 42, wherein the stimulus comprises the plurality of stimuli of any one of the preceding clauses.

Clause 44. The method of clause 42, wherein the pupil is dilated with a mydriatic.

Clause 45. The method of clause 44, wherein the mydriatic comprises a cycloplegic an optionally wherein the cycloplegic is selected from the group consisting of atropine, cyclopentolate, homatropine, scopolamine and tropicamide.

Clause 46. The method of clause 45, wherein the cycloplegic comprises atropine with a percentage by weight within a range from 0.025% to 0.2% and optionally from 0.05% to 0.1%.

Clause 47. The method of clause 42, wherein a size of the pupil is measured and the optical stimulus is directed toward the eye in response to the size of the pupil and optionally wherein the size of the pupil comprises a diameter of the pupil.

Clause 48. The method of clause 47, wherein one or more of an intensity or a duration of the optical stimulus is adjusted in response to the size of the pupil.

Clause 49. The method of clause 47, wherein the size of the pupil is measured with a sensor and optionally wherein the sensor comprises a sensor array and optionally wherein the sensor array comprises a sensor array of a camera.

Clause 50. The method of clause 42, wherein the pupil comprises natural pupil of the eye dilated with an appropriate amount of illumination of the peripheral retina and light from other sources passing through the natural pupil and optionally wherein the natural pupil is capable of constricting and dilating in response to illumination to the eye.

Clause 51. The method of clause 50, wherein the natural pupil is dilated with a mesopic background illumination or a scotopic background illumination and optionally wherein the mesopic background illumination comprises an amount within a range from 0.01 Candela per square meter (cd/m2) to 3 cd/m2.

Clause 52. The method of clause 51, wherein the natural pupil constricts by no more than one millimeter (mm) when the stimulus is provided as compared to a diameter of the natural pupil when the stimulus has not yet been provided.

Clause 53. The method of clause 51, wherein the natural pupil comprises a stimulation diameter when the eye is exposed to the stimulus and wherein the natural pupil comprises a photopic diameter when the eye is exposed to photopic viewing conditions, and wherein the photopic diameter is at least one millimeter smaller than the stimulation diameter.

Clause 54. The method of clause 42, wherein the stimulus is configured to illuminate the peripheral retina with an eccentricity of greater than 35 degrees with the pupil dilated by at least about 1 millimeter as compared to photopic illumination while the stimulus is provided to the peripheral retina with the eccentricity of greater than 35 degrees.

Clause 55. The method of clause 42, wherein no more than 10% of a total amount of energy of the plurality of stimuli is directed to a fovea of the eye in order to decrease constriction of the pupil in response to the plurality of stimuli and optionally no more than 5% of the total amount and optionally no more than 1% of the total amount.

Clause 56. The method of clause 42, wherein the stimulus comprises a photopic stimulus directed to the peripheral regions of the retina and wherein illumination of one or more of the fovea or macula comprises one or more of mesopic or scotopic illumination in order to decrease a size of the pupil.

Embodiments of the present disclosure have been shown and described as set forth herein and are provided by way of example only. One of ordinary skill in the art will recognize numerous adaptations, changes, variations and substitutions without departing from the scope of the present disclosure. Several alternatives and combinations of the embodiments disclosed herein may be utilized without departing from the scope of the present disclosure and the inventions disclosed herein. Therefore, the scope of the presently disclosed inventions shall be defined solely by the scope of the appended claims and the equivalents thereof.

What is claimed is:

1. An apparatus for treating refractive error of an eye, the apparatus comprising:
    a plurality of stimuli;
    one or more optics to image the plurality of stimuli anterior or posterior to a peripheral portion of the retina to form a plurality of defocused images on the peripheral portion of the retina; and
    a sensor to measure a size of a pupil and further comprising a processor configured with instructions to direct the plurality of stimuli toward the eye in response to the size of the pupil;
    wherein the plurality of stimuli and the one or more optics are arranged to reduce hindrance to a central vision of the eye;
    wherein the processor is configured to adjust one or more of an intensity or a duration of the plurality of stimuli in response to the size of the pupil;
    wherein the plurality of stimuli is configured to illuminate the peripheral portion of the retina with an eccentricity of greater than 35 degrees and configured to allow the pupil of the eye to dilate by at least about 1 millimeter while the plurality of stimuli is provided to the peripheral portion of the retina with the eccentricity of greater than 35 degrees.

2. The apparatus of claim 1, wherein the apparatus is configured to provide a background illumination and wherein a brightness of said plurality of defocused images is higher than a brightness of the background illumination by a factor of at least 3.

3. The apparatus of claim 1, wherein each of said plurality of defocused images comprises an intensity profile distribution, each intensity profile distribution comprising one or more peaks distributed around an inner portion with a decreased intensity relative to the one or more peaks.

4. The apparatus of claim 3, wherein the one or more peaks comprises a plurality of peaks and wherein the inner portion is located between the plurality of peaks.

5. The apparatus of claim 4, wherein the plurality of peaks comprises four peaks and the inner portion is located between the four peaks.

6. The apparatus of claim 5, wherein the inner portion comprises a cross extending between the four peaks.

7. The apparatus of claim 3, wherein the one or more peaks comprises an annular peak and wherein the inner portion is located within the annular peak.

8. The apparatus of claim 1, wherein each of said plurality of defocused images comprises a polychromatic icon on a darker background to provide contrast.

9. The apparatus of claim 1, the plurality of stimuli and the one or more optics are arranged to provide a substantially uninterrupted field of view within a range from 10 degrees to 30 degrees.

10. The apparatus of claim 1, wherein each of the plurality of stimuli comprises a global contrast factor greater than 0.7.

11. The apparatus of claim 1, wherein the one or more optics are arranged to project the plurality of stimuli toward the peripheral portion of the retina when the pupil of the eye has been dilated with a mydriatic.

12. The apparatus of claim 1, wherein the plurality of stimuli is arranged to illuminate the peripheral portion of the retina at an angle of at least 35 degrees from a visual axis of the eye.

13. The apparatus of claim 1, wherein the sensor comprises a sensor array.

14. The apparatus of claim 1, wherein the plurality of stimuli is configured to allow dilation of a natural pupil when illuminated with plurality of stimuli.

15. The apparatus of claim 1, wherein the plurality of stimuli is configured to constrict the pupil by no more than one millimeter (mm) when the plurality of stimuli is provided as compared to a diameter of the pupil when the plurality of stimuli has not yet been provided.

16. The apparatus of claim 1, wherein the pupil comprises a stimulation diameter when the eye is exposed to the plurality of stimuli and wherein the eye comprises a photopic diameter when the eye is exposed to photopic viewing conditions without the plurality of stimuli, and wherein the photopic diameter is at least one millimeter smaller than the stimulation diameter.

17. The apparatus of claim 1, wherein no more than 10% of a total amount of energy of the plurality of stimuli is directed to a fovea of the eye in order to decrease constriction of the pupil in response to the plurality of stimuli.

* * * * *